United States Patent
Nishida et al.

(10) Patent No.: US 12,296,015 B2
(45) Date of Patent: May 13, 2025

(54) AQUEOUS LIQUID PREPARATION

(71) Applicant: SENJU USA, INC., Torrance, CA (US)

(72) Inventors: Yumena Nishida, Osaka (JP); Yuki Nakamura, Osaka (JP); Tatsuya Sakai, Osaka (JP)

(73) Assignee: SENJU USA, INC., Torrance, CA (US)

(*) Notice: Subject to any disclaimer, the term of this patent is extended or adjusted under 35 U.S.C. 154(b) by 0 days.

(21) Appl. No.: 18/659,629

(22) Filed: May 9, 2024

(65) Prior Publication Data

US 2024/0307544 A1 Sep. 19, 2024

Related U.S. Application Data

(63) Continuation-in-part of application No. PCT/JP2023/001725, filed on Jan. 20, 2023.

(30) Foreign Application Priority Data

Jan. 21, 2022 (JP) ................................. 2022-007774

(51) Int. Cl.
| | | |
|---|---|---|
| *A61K 47/38* | (2006.01) | |
| *A61K 9/00* | (2006.01) | |
| *A61K 9/08* | (2006.01) | |
| *A61K 31/7036* | (2006.01) | |
| *A61K 47/32* | (2006.01) | |
| *A61P 27/02* | (2006.01) | |
| *A61P 31/04* | (2006.01) | |

(52) U.S. Cl.
CPC ............ *A61K 47/38* (2013.01); *A61K 9/0048* (2013.01); *A61K 9/08* (2013.01); *A61K 31/7036* (2013.01); *A61K 47/32* (2013.01); *A61P 27/02* (2018.01); *A61P 31/04* (2018.01)

(58) Field of Classification Search
CPC .. A61K 47/38; A61K 9/0048; A61K 31/7036; A61K 47/32; A61P 27/02; A61P 31/04
See application file for complete search history.

(56) References Cited

U.S. PATENT DOCUMENTS

| | | |
|---|---|---|
| 9,511,143 B2 | 12/2016 | Keller et al. |
| 2007/0082857 A1 | 4/2007 | Sawa |
| 2007/0270378 A1 | 11/2007 | Sakamoto et al. |
| 2010/0311688 A1 * | 12/2010 | Chapin ................... A61K 47/38 514/57 |
| 2012/0027716 A1 | 2/2012 | Stein et al. |
| 2012/0195972 A1 * | 8/2012 | Abelson ............. A61K 31/7034 206/572 |
| 2014/0343005 A1 | 11/2014 | Keller et al. |
| 2020/0016176 A1 | 1/2020 | Nguyen |

FOREIGN PATENT DOCUMENTS

| | | |
|---|---|---|
| CN | 106420811 | 2/2017 |
| CN | 106474149 | 3/2017 |
| JP | 56-51499 | 5/1981 |
| JP | 58-134099 | 8/1983 |
| JP | 2002-97129 | 4/2002 |
| JP | 2006-89460 | 4/2006 |
| JP | 2013-528589 | 7/2013 |
| JP | 2021-35984 | 3/2021 |
| WO | 2005/046700 | 5/2005 |
| WO | 2011/140194 | 11/2011 |

OTHER PUBLICATIONS

International Search Report issued May 9, 2023 in International (PCT) Application No. PCT/JP2023/001725.
Tetsuya Matsumoto "Arbekacin: another novel agent for treating infections due to methicillin-resistant *Staphylococcus aureus* and multidrug-resistant Gram-negative pathogens", Clinical Pharmacology, 2014, vol. 26, No. 6, pp. 139-148.
Hassan et al., "A Simple Rheological Method for the in Vitro Assessment of Mucin-Polymer Bioadhesive Bond Strength", Pharmaceutical Research, 1990, vol. 7, No. 5, pp. 491-495.
Craig et al., "TFOS DEWS II Report Executive Summary", The Ocular Surface, 2017, pp. 1-11.
Boddeda et al., "A Review on Mucoadhesive Polymers in Ophthalmics", Int. J. Pharm. Sci. Rev. Res., 2014, vol. 24, No. 1, pp. 237-245.
Hori, "Special Feature: Dry Eye—A Close Look at the Mechanism of Eye Dryness—", Journal of the Eye, 2005, vol. 22, No. 3, pp. 289-294, with English translation.
Li et al., "Expression of mucins MUC5AC and MUC19 on the ocular surface in dry eye syndrome model of ovariectomized female rabbits", Adv Clin Exp Med., 2019, vol. 28, No. 2, pp. 165-169.
Zhang et al., "Analysis of tear film rupture: effect of non-Newtonian rheology", Journal of Colloid and Interface Science, 2003, vol. 262, No. 1, pp. 130-148.
Davidson et al., "The tear film and ocular mucins", Veterinary Ophthalmology, 2004, vol. 7, No. 2, pp. 71-77.

(Continued)

*Primary Examiner* — Zohreh A Fay

(74) *Attorney, Agent, or Firm* — Wenderoth, Lind & Ponack, L.L.P.

(57) ABSTRACT

Provided is an aqueous liquid preparation comprising arbekacin and/or a salt thereof and at least one water-soluble polymer selected from the group consisting of hydroxypropyl methylcellulose, hydroxyethyl cellulose, methyl cellulose, and polyvinylpyrrolidone.

11 Claims, 1 Drawing Sheet

(56) References Cited

OTHER PUBLICATIONS

Li et al., "Solution viscosity effects on the ocular disposition of cromolyn sodium in the albino rabbit", International Journal of Pharmaceutics, 1989, vol. 53, No. 3, pp. 219-225.
Clinical Ophthalmology, 2021, vol. 75, No. 11, cited in the specification, paragraph [0083].
Guidelines for Infectious Keratitis Treatment (second edition), Japanese Ophthalmological Society, 2013, cited in the specification, paragraph [0083].
Notice of Reasons for Refusal issued Nov. 14, 2023 in Japanese Patent Application No. 2023-554283, with English translation.

\* cited by examiner

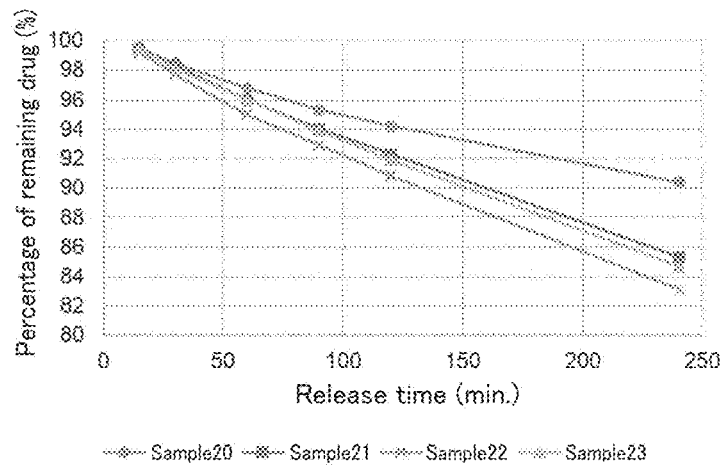
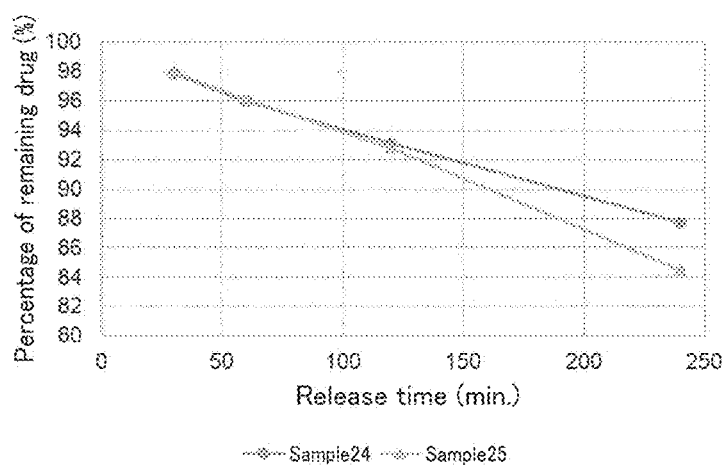
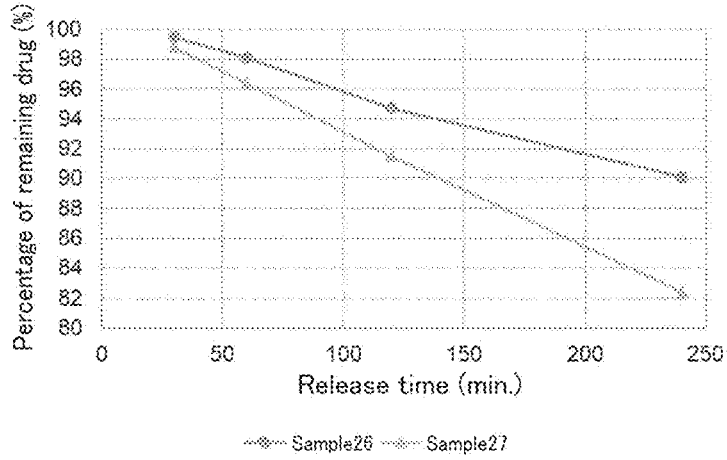

AQUEOUS LIQUID PREPARATION

TECHNICAL FIELD

The present invention relates to an aqueous liquid preparation comprising arbekacin and/or a salt thereof and at least one water-soluble polymer selected from the group consisting of hydroxypropyl methylcellulose, hydroxyethyl cellulose, methyl cellulose, and polyvinylpyrrolidone; and application techniques etc. thereof.

BACKGROUND ART

Arbekacin is one of the aminoglycoside antibiotics. Arbekacin sulfate is used to treat pneumonia and sepsis caused by methicillin-resistant *Staphylococcus aureus* (MRSA) (Patent Literature (PTL) 1). Arbekacin sulfate has been reported to have a broad-spectrum antibacterial activity against gram-negative bacteria, as well as gram-positive bacteria such as methicillin-resistant *Staphylococcus aureus* (Non-patent Literature (NPL) 1).

In aqueous liquid preparations, water-soluble polymers, such as hydroxypropyl methylcellulose, 2-hydroxypropyl-β-cyclodextrin, hydroxyethylcellulose, and dextran, are commonly used, for example, as thickening agents or thickeners (PTL 2 and PTL 3).

CITATION LIST

Patent Literature

PTL 1: U.S. Pat. No. 9,511,143
PTL 2: U.S. Patent Application Publication No. 2020/0016176
PTL 3: U.S. Patent Application Publication No. 2007/0270378

Non-Patent Literature

NPL 1: *Clin. Pharmacol.* 2014 Sep. 26; 6: 139-48.
NPL 2: *Pharm. Res.* 1990 May; 7(5): 491-5.
NPL 3: TFOSDEWS II Report Executive Summary, *The Ocular Surface* (2017), http://dx.doi.org/10.1016/j.jtos.2017.08.003
NPL 4: *Int. J. Pharm. Sci. Rev. Res.* 2014, 24 (1), 237-245.
NPL 5: *Journal of the Eye, Vol.* 22, No. 3, 2005, 289-294.
NPL 6: *Adv. Clin. Exp. Med.* 2019; 28 (2): 165-169.
NPL 7: *J. Colloid Interface Sci.* 2003 Jun. 1; 262 (1): 130-48.
NPL 8: *Vet. Ophthalmol.* March-April 2004; 7(2): 71-7.
NPL 9: *International Journal of Pharmaceutics,* 1989; 53(3): 219-225

SUMMARY OF INVENTION

Technical Problem

An object of the present disclosure is to provide a formulation technique that relates to an aqueous liquid preparation comprising arbekacin and/or a salt thereof and at least one water-soluble polymer selected from the group consisting of hydroxypropyl methylcellulose, hydroxyethyl cellulose, methyl cellulose, and polyvinylpyrrolidone.

Solution to Problem

The present inventors found that an aqueous liquid preparation comprising arbekacin and/or a salt thereof and at least one water-soluble polymer selected from the group consisting of hydroxypropyl methylcellulose, hydroxyethyl cellulose, methyl cellulose, and polyvinylpyrrolidone has excellent mucin adhesion, and made further improvements based on this finding.

Specifically, the present invention includes, for example, the subject matter described in the following items.

Item 1-1.
An aqueous liquid preparation comprising
arbekacin and/or a salt thereof and
at least one water-soluble polymer selected from the group consisting of hydroxypropyl methylcellulose, hydroxyethyl cellulose, methyl cellulose, and polyvinylpyrrolidone.

Item 1-2.
The aqueous liquid preparation according to Item 1-1, wherein the total concentration of the arbekacin and/or a salt thereof is about 0.05 w/v % to about 5.0 w/v %.

Item 1-3.
The aqueous liquid preparation according to Item 1-1 or Item 1-2, wherein the total concentration of the arbekacin and/or a salt thereof is about 0.1 w/v % to about 3.0 w/v %.

Item 1-4.
The aqueous liquid preparation according to any one of Items 1-1 to 1-3, wherein the water-soluble polymer comprises hydroxypropyl methylcellulose.

Item 1-5.
The aqueous liquid preparation according to any one of Items 1-1 to 1-4, wherein the concentration of the water-soluble polymer is about 0.05 w/v % to about 8.8 w/v %.

Item 1-6.
The aqueous liquid preparation according to any one of Items 1-1 to 1-5, wherein the concentration of the water-soluble polymer is about 0.3 w/v % to about 2.0 w/v %.

Item 1-7.
The aqueous liquid preparation according to any one of Items 1-1 to 1-6, wherein the concentration of the water-soluble polymer is about 0.8 w/v % to about 1.4 w/v %.

Item 1-8.
An aqueous liquid preparation comprising arbekacin and/or a salt thereof and hydroxypropyl methyl cellulose, wherein
the total concentration of the arbekacin and/or a salt thereof is about 0.1 w/v % to about 3.0 w/v %; and
the concentration of the hydroxypropyl methylcellulose is about 0.8 w/v % to about 1.4 w/v %.

Item 1-9.
The aqueous liquid preparation according to any one of Items 1-1 to 1-8, wherein the mass ratio of the total content of the arbekacin and/or a salt thereof to the content of the water-soluble polymer is in the range of about 1:0.04 to about 1:70.

Item 1-10.
The aqueous liquid preparation according to any one of Items 1-1 to 1-9, wherein the mass ratio of the total content of the arbekacin and/or a salt thereof to the content of the water-soluble polymer is in the range of about 1:0.1 to about 1:20.

Item 1-11.
The aqueous liquid preparation according to any one of Items 1-1 to 1-10, wherein the mass ratio of the total content of the arbekacin and/or a salt thereof to the content of the water-soluble polymer is in the range of about 1:0.25 to about 1:14.

Item 1-12.
The aqueous liquid preparation according to any one of Items 1-1 to 1-11, wherein the aqueous liquid preparation has a pH of about 5.0 to about 8.0.

Item 1-13.
The aqueous liquid preparation according to any one of Items 1-1 to 1-12, wherein the aqueous liquid preparation has a viscosity of about 5 to about 50 mPa·s.

Item 1-14.
An aqueous liquid preparation comprising arbekacin and/or a salt thereof and hydroxypropyl methyl cellulose, wherein
- the total concentration of the arbekacin and/or a salt thereof is about 0.1 w/v % to about 3.0 w/v %;
- the concentration of the hydroxypropyl methylcellulose is about 0.3 w/v % to about 2.0 w/v %;
- the mass ratio of the total content of the arbekacin and/or a salt thereof to the content of the water-soluble polymer is in the range of about 1:0.04 to about 1:70;
- the aqueous liquid preparation has a pH of about 5.0 to about 8.0; and
- the aqueous liquid preparation has a viscosity of about 5 to about 50 mPa·s.

Item 1-15.
The aqueous liquid preparation according to any one of Items 1-1 to 1-14, wherein $$C - (A + B) > 0$$

wherein
- A: viscosity increase value (mPa·s) achieved by arbekacin;
- B: viscosity increase value (mPa·s) achieved by a water-soluble polymer; and
- C: viscosity increase value (mPa·s) achieved by arbekacin+a water-soluble polymer; and Viscosity increase value (mPa·s) = $(\eta_1 - \eta_2) - \eta_3$ wherein
- $\eta_1$: viscosity of a mixture of a solution (1 mL) containing arbekacin and/or a water-soluble polymer at the concentration in the aqueous liquid preparation and a 6 w/v % mucin solution (1 mL);
- $\eta_2$: viscosity of a mixture of a solution (1 mL) containing arbekacin and/or a water-soluble polymer at the concentration in the aqueous liquid preparation and a 0.1M phosphate buffer (1 mL); and
- $\eta_3$: viscosity of a mixture of a 0.1M phosphate buffer (1 mL) and a 6 w/v % mucin solution (1 mL).

Item 1-16.
The aqueous liquid preparation according to any one of Items 1-1 to 1-15, wherein C−(A+B)>0.1.

Item 1-17.
The aqueous liquid preparation according to any one of Items 1-1 to 1-16, wherein C−(A+B)>0.5.

Item 1-18.
An aqueous liquid preparation comprising arbekacin and/or a salt thereof and hydroxypropyl methyl cellulose, wherein
- the total concentration of the arbekacin and/or a salt thereof is about 0.1 w/v % to about 3.0 w/v %;
- the concentration of the hydroxypropyl methylcellulose is about 0.3 w/v % to about 2.0 w/v %;
- the mass ratio of the total content of the arbekacin and/or a salt thereof to the content of the water-soluble polymer is in the range of about 1:0.04 to about 1:70;
- the aqueous liquid preparation has a pH of about 5.0 to about 8.0;
- the aqueous liquid preparation has a viscosity of about 5 to about 50 mPa·s; and $$C - (A + B) > 0$$

wherein
- A: viscosity increase value (mPa·s) achieved by arbekacin;
- B: viscosity increase value (mPa·s) achieved by a water-soluble polymer; and
- C: viscosity increase value (mPa·s) achieved by arbekacin+a water-soluble polymer; and Viscosity increase value (mPa·s)=$(\eta_1-\eta_2)-\eta_3$ wherein
- $\eta_1$: viscosity of a mixture of a solution (1 mL) containing arbekacin and/or a water-soluble polymer at the concentration in the aqueous liquid preparation and a 6 w/v % mucin solution (1 mL);
- $\eta_2$: viscosity of a mixture of a solution (1 mL) containing arbekacin and/or a water-soluble polymer at the concentration in the aqueous liquid preparation and a 0.1M phosphate buffer (1 mL); and
- $\eta_3$: viscosity of a mixture of a 0.1M phosphate buffer (1 mL) and a 6 w/v % mucin solution (1 mL).

Item 1-19.
The aqueous liquid preparation according to any one of Items 1-1 to 1-18, wherein the decrease percentage in the release rate of arbekacin and/or a salt thereof is 5% or more.

Item 1-20.
The aqueous liquid preparation according to any one of Items 1-1 to 1-19, wherein the decrease percentage in the release rate of arbekacin and/or a salt thereof is 25% or more.

Item 1-21.
The aqueous liquid preparation according to any one of Items 1-1 to 1-20, which is an ophthalmic solution.

Item 1-22.
The aqueous liquid preparation according to any one of Items 1-1 to 1-21, which is for use in thickening the aqueous liquid solution containing the water-soluble polymer on the ocular surface.

Item 1-23.
The aqueous liquid preparation according to any one of Items 1-1 to 1-22, which is for use in enhancing mucin adhesion.

Item 1-24.
The aqueous liquid preparation according to any one of Items 1-1 to 1-23, which is for use in tear film stabilization.

Item 1-25.
The aqueous liquid preparation according to any one of Items 1-1 to 1-24, which is for use in improving transferability of arbekacin to the conjunctiva.

Item 1-26.
The aqueous liquid preparation according to any one of Items 1-1 to 1-25, which is for use in the treatment of bacterial external ocular infection.

Item 1-27.

The aqueous liquid preparation according to any one of Items 1-1 to 1-26, which is for use in the treatment of bacterial keratoconjunctivitis.

Item 1-28.

The aqueous liquid preparation according to any one of Items 1-1 to 1-27, which is for use in the treatment of bacterial conjunctivitis.

Item 1-29.

The aqueous liquid preparation according to any one of Items 1-1 to 1-28, wherein the bacterium is a gram-positive bacterium or a gram-negative bacterium.

Item 1-30.

The aqueous liquid preparation according to any one of Items 1-1 to 1-29, wherein the bacterium is selected from the group consisting of methicillin-resistant *Staphylococcus aureus, Staphylococcus, Corynebacterium, Pseudomonas aeruginosa, Haemophilus influenzae, Streptococcus pneumoniae, Moraxella, Neisseria gonorrhoeae, Serratia, Streptococcus, Anaerobes*, atypical mycobacteria, and *Streptococcus pneumoniae*.

Item 1-31.

The aqueous liquid preparation according to any one of Items 1-1 to 1-30, which is for use in the treatment of dry eye.

Item 1-32.

The aqueous liquid preparation according to any one of Items 1-1 to 1-31, which is for use in the treatment of bacterial external ocular infection with dry eye.

Item 1-33.

The aqueous liquid preparation according to any one of Items 1-1 to 1-32, which is for use in the treatment of bacterial keratoconjunctivitis with dry eye.

Item 1-34.

The aqueous liquid preparation according to any one of Items 1-1 to 1-33, which is for use in the treatment of bacterial conjunctivitis with dry eye.

Item 1-35.

An aqueous liquid preparation comprising arbekacin and/or a salt thereof and hydroxypropyl methyl cellulose, which is for use in the treatment of bacterial external ocular infection with dry eye.

Item 1-36.

An aqueous liquid preparation comprising arbekacin and/or a salt thereof and hydroxypropyl methyl cellulose, the aqueous liquid preparation being for use in the treatment of bacterial external ocular infection with dry eye.

Item 2-1.

A method for treating bacterial external ocular infection, comprising administering an aqueous liquid preparation comprising arbekacin and/or a salt thereof and at least one water-soluble polymer to a subject in need thereof, the water-soluble polymer comprising at least one member selected from the group consisting of hydroxypropyl methylcellulose, hydroxyethylcellulose, methylcellulose, and polyvinylpyrrolidone.

Item 2-2.

A method for treating bacterial external ocular infection, comprising administering an aqueous liquid preparation comprising arbekacin and/or a salt thereof and at least one water-soluble polymer to a subject in need thereof, the water-soluble polymer comprising hydroxypropyl methylcellulose.

Item 2-3.

A method for treating bacterial conjunctivitis, comprising administering an aqueous liquid preparation comprising arbekacin and/or a salt thereof and at least one water-soluble polymer to a subject in need thereof, the water-soluble polymer comprising hydroxypropyl methylcellulose.

Item 2-4.

A method for treating bacterial external ocular infection, comprising administering an aqueous liquid preparation comprising arbekacin and/or a salt thereof and at least one water-soluble polymer to the ocular surface of a subject in need thereof, the water-soluble polymer comprising at least one member selected from the group consisting of hydroxypropyl methylcellulose, hydroxyethylcellulose, methylcellulose, and polyvinylpyrrolidone.

Item 2-5.

A method for treating bacterial conjunctivitis, comprising administering an aqueous liquid preparation comprising arbekacin and/or a salt thereof and hydroxypropyl methyl cellulose to the ocular surface of a subject in need thereof.

Item 2-6a.

The treatment method according to any one of Items 2-1 to 2-5, comprising allowing the aqueous liquid preparation to be in contact with mucin.

Item 2-6b.

The treatment method according to any one of Items 2-1 to 2-5, wherein administering the aqueous liquid preparation to the ocular surface of a subject in need thereof is a step of administration to the ocular surface of the subject so as to allow the aqueous liquid preparation to be in contact with mucin.

Item 2-7a.

The treatment method according to any one of Items 2-1 to 2-6, comprising increasing the viscosity of the aqueous liquid preparation on the ocular surface.

Item 2-7b.

The treatment method according to any one of Items 2-1 to 2-6, wherein administering the aqueous liquid preparation to the ocular surface of a subject in need thereof is a step of administration to the ocular surface of the subject so as to thicken the aqueous liquid preparation on the ocular surface.

Item 2-8a.

The treatment method according to any one of Items 2-1 to 2-7, comprising enhancing adhesion to mucin.

Item 2-8b.

The treatment method according to any one of Items 2-1 to 2-7, wherein administering the aqueous liquid preparation to the ocular surface of a subject in need thereof is a step of administration to the ocular surface of the subject so as to enhance adhesion of the aqueous liquid preparation to mucin after the administration.

Item 2-9a.

A method for treating bacterial external ocular infection, comprising
   administering an aqueous liquid preparation comprising arbekacin and/or a salt thereof and at least one water-soluble polymer to the ocular surface of a subject in need thereof; and
   allowing the aqueous liquid preparation to be in contact with mucin to thicken the aqueous liquid preparation, thereby enhancing adhesion of the aqueous liquid preparation to mucin,
the water-soluble polymer comprising at least one member selected from the group consisting of hydroxypropyl methylcellulose, hydroxyethylcellulose, methylcellulose, and polyvinylpyrrolidone.

Item 2-9b.

A method for treating bacterial external ocular infection, comprising administering an aqueous liquid preparation comprising arbekacin and/or a salt thereof and at least one water-soluble polymer to the ocular surface of a subject in need thereof, wherein
- the water-soluble polymer comprises at least one member selected from the group consisting of hydroxypropyl methylcellulose, hydroxyethylcellulose, methylcellulose, and polyvinylpyrrolidone, and
- the administering is performed so as to allow the aqueous liquid preparation to be in contact with mucin and thereby thicken the aqueous liquid preparation and enhance adhesion of the aqueous liquid preparation to mucin.

Item 2-9c.

A method for treating bacterial conjunctivitis, comprising
- administering an aqueous liquid preparation comprising arbekacin and/or a salt thereof and hydroxypropyl methyl cellulose to the ocular surface of a subject in need thereof; and
- allowing the aqueous liquid preparation to be in contact with mucin to thicken the aqueous liquid preparation, thereby enhancing adhesion of the aqueous liquid preparation to mucin.

Item 2-9d.

A method for treating bacterial conjunctivitis, comprising administering an aqueous liquid preparation comprising arbekacin and/or a salt thereof and hydroxypropyl methyl cellulose to the ocular surface of a subject in need thereof, wherein the administering is performed so as to allow the aqueous liquid preparation to be in contact with mucin and thereby thicken the aqueous liquid preparation, thus enhancing adhesion of the aqueous liquid preparation to mucin.

Item 2-10.

A method for improving transferability of arbekacin and/or a salt thereof to the conjunctiva, comprising administering an aqueous liquid preparation comprising arbekacin and/or a salt thereof and at least one aqueous polymer to a subject in need thereof, the aqueous polymer comprising hydroxypropyl methyl cellulose.

Item 2-11.

The method according to any one of Items 2-1 to 2-10, wherein the total concentration of the arbekacin and/or a salt thereof in the aqueous liquid preparation is about 0.05 w/v % to about 5.0 w/v %.

Item 2-12.

The method according to any one of Items 2-1 to 2-11, wherein the concentration of the water-soluble polymer in the aqueous liquid preparation is about 0.05 w/v % to about 8.8 w/v %.

Item 2-13.

The method according to any one of Items 2-1 to 2-12, wherein the mass ratio of the total content of the arbekacin and/or a salt thereof to the content of the water-soluble polymer in the aqueous liquid preparation is in the range of about 1:0.04 to about 1:70.

Item 2-14.

The method according to any one of Items 2-1 to 2-13, wherein the aqueous liquid preparation has a pH of about 5.0 to about 8.0.

Item 2-15.

The method according to any one of Items 2-1 to 2-14, wherein the aqueous liquid preparation has a viscosity of about 5 to about 50 mPa·s.

Item 2-16.

A method for treating bacterial external ocular infection, comprising administering an aqueous liquid preparation comprising arbekacin and/or a salt thereof and at least one water-soluble polymer to a subject in need thereof, wherein
- the aqueous polymer comprises hydroxypropyl methyl cellulose;
- the total concentration of the arbekacin and/or a salt thereof is about 0.1 w/v % to about 3.0 w/v %;
- the concentration of the hydroxypropyl methylcellulose is about 0.3 w/v % to about 2.0 w/v %;
- the mass ratio of the total content of the arbekacin and/or a salt thereof to the content of the water-soluble polymer is in the range of about 1:0.04 to about 1:70;
- the aqueous liquid preparation has a pH of about 5.0 to about 8.0; and
- the aqueous liquid preparation has a viscosity of about 5 to about 50 mPa·s.

Item 2-17.

The method according to any one of Items 2-1 to 2-16, wherein $$[C - (A + B)] > 0$$

wherein
- A: viscosity increase value (mPa·s) achieved by arbekacin;
- B: viscosity increase value (mPa·s) achieved by the water-soluble polymer; and
- C: viscosity increase value (mPa·s) achieved by arbekacin and the water-soluble polymer; and
- Viscosity increase value (mPa·s)=$(\eta_1-\eta_2)-\eta_3$ wherein
  - $\eta_1$: viscosity of a mixture of a solution (1 mL) containing arbekacin and/or a water-soluble polymer at the concentration in the aqueous liquid preparation and a 6 w/v % mucin solution (1 mL);
  - $\eta_2$: viscosity of a mixture of a solution (1 mL) containing arbekacin and/or a water-soluble a polymer at the concentration in the aqueous liquid preparation and a 0.1M phosphate buffer (1 mL); and
  - $\eta_3$: viscosity of a mixture of a 0.1M phosphate buffer (1 mL) and a 6 w/v % mucin solution (1 mL).

Item 2-18.

The method according to any one of Items 2-1 to 2-17, wherein the aqueous liquid preparation has a decrease percentage in the release rate of arbekacin and/or a salt thereof of 5% or more.

Item 2-19.

The method according to any one of Items 2-1 to 2-18, wherein the aqueous liquid preparation is an ophthalmic solution.

Item 2-20a.

A method for treating bacterial conjunctivitis, comprising administering an aqueous liquid preparation comprising arbekacin and/or a salt thereof and at least one water-soluble polymer to a subject in need thereof to allow the aqueous liquid preparation to be in contact with mucin, wherein
- the water-soluble polymer comprises hydroxypropyl methyl cellulose;
- the total concentration of the arbekacin and/or a salt thereof is about 0.1 w/v % to about 3.0 w/v %;
- the concentration of the hydroxypropyl methylcellulose is about 0.3 w/v % to about 2.0 w/v %;
- the mass ratio of the total content of the arbekacin and/or a salt thereof to the content of the water-soluble polymer is in the range of about 1:0.04 to about 1:70;
- the aqueous liquid preparation has a pH of about 5.0 to about 8.0; and
- the aqueous liquid preparation has a viscosity of about 5 to about 50 mPa·s.

Item 2-20b.

A method for treating bacterial conjunctivitis, comprising administering an aqueous liquid preparation comprising arbekacin and/or a salt thereof and at least one water-soluble polymer to a subject in need thereof so as to allow the aqueous liquid preparation to be in contact with mucin, wherein
   the water-soluble polymer comprises hydroxypropyl methyl cellulose;
   the total concentration of the arbekacin and/or a salt thereof is about 0.1 w/v % to about 3.0 w/v %;
   the concentration of the hydroxypropyl methylcellulose is about 0.3 w/v % to about 2.0 w/v %;
   the mass ratio of the total content of the arbekacin and/or a salt thereof to the content of the water-soluble polymer is in the range of about 1:0.04 to about 1:70;
   the aqueous liquid preparation has a pH of about 5.0 to about 8.0; and
   the aqueous liquid preparation has a viscosity of about 5 to about 50 mPa·s.

Item 3-1.

A method for treating bacterial external ocular infection with dry eye, comprising administering an aqueous liquid preparation comprising arbekacin and/or a salt thereof and at least one water-soluble polymer to a subject in need thereof, the water-soluble polymer comprising at least one member selected from the group consisting of hydroxypropyl methylcellulose, hydroxyethylcellulose, methylcellulose, and polyvinylpyrrolidone.

Item 3-2.

A method for treating bacterial external ocular infection with dry eye, comprising administering an aqueous liquid preparation comprising arbekacin and/or a salt thereof and at least one water-soluble polymer to a subject in need thereof, the aqueous polymer comprising hydroxypropyl methylcellulose.

Item 3-3.

A method for treating bacterial conjunctivitis with dry eye, comprising administering an aqueous liquid preparation comprising arbekacin and/or a salt thereof and at least one water-soluble polymer to a subject in need thereof, the aqueous polymer comprising hydroxypropyl methylcellulose.

Item 3-4.

The treatment method according to any one of Items 3-1 to 3-3, wherein the total concentration of the arbekacin and/or a salt thereof in the aqueous liquid preparation is about 0.05 w/v % to about 5.0 w/v %.

Item 3-5.

The treatment method according to any one of Items 3-1 to 3-4, wherein the concentration of the water-soluble polymer in the aqueous liquid preparation is about 0.05 w/v % to about 8.8 w/v %.

Item 3-6.

The treatment method according to any one of Items 3-1 to 3-5, wherein the mass ratio of the total content of the arbekacin and/or a salt thereof to the content of the water-soluble polymer is in the range of about 1:0.04 to about 1:70.

Item 3-7.

The treatment method according to any one of Items 3-1 to 3-6, wherein the aqueous liquid preparation has a pH of about 5.0 to about 8.0.

Item 3-8.

The treatment method according to any one of Items 3-1 to 3-7, wherein the aqueous liquid preparation has a viscosity of about 5 to about 50 mPa·s.

Item 3-9.

A method for treating bacterial external ocular infection with dry eye, comprising administering an aqueous liquid preparation comprising arbekacin and/or a salt thereof and at least one water-soluble polymer to a subject in need thereof, wherein
   the water-soluble polymer comprises hydroxypropyl methylcellulose;
   the total concentration of the arbekacin and/or a salt thereof is about 0.1 w/v % to about 3.0 w/v %;
   the concentration of the hydroxypropyl methylcellulose is about 0.3 w/v % to about 2.0 w/v %;
   the mass ratio of the total content of the arbekacin and/or a salt thereof to the content of the water-soluble polymer is in the range of about 1:0.04 to about 1:70;
   the aqueous liquid preparation has a pH of about 5.0 to about 8.0; and
   the aqueous liquid preparation has a viscosity of about 5 to about 50 mPa·s.

Item 3-10.

The treatment method according to any one of Items 3-1 to 3-9, wherein the aqueous liquid preparation is an aqueous liquid preparation, wherein $$[C - (A + B)] > 0$$

wherein
   A represents a viscosity increase value (mPa·s) achieved by arbekacin;
   B represents a viscosity increase value (mPa·s) achieved by the water-soluble polymer; and
   C represents a viscosity increase value (mPa·s) achieved by arbekacin+the water-soluble polymer; and
   Viscosity increase value (mPa·s)=$(\eta_1-\eta_2)-\eta_3$ wherein
   $\eta_1$: viscosity of a mixture of a solution (1 mL) containing arbekacin and/or a water-soluble polymer at the concentration in the aqueous liquid preparation and a 6 w/v % mucin solution (1 mL);
   $\eta_2$: viscosity of a mixture of a solution (1 mL) containing arbekacin and/or a water-soluble polymer at the concentration in the aqueous liquid preparation and a 0.1M phosphate buffer (1 mL); and
   $\eta_3$: viscosity of a mixture of a 0.1M phosphate buffer (1 mL) and a 6 w/v % mucin solution (1 mL).

Item 3-11.

The treatment method according to any one of Items 3-1 to 3-10, wherein the aqueous liquid preparation has a decrease percentage in the release rate of arbekacin and/or a salt thereof of 5% or more.

Item 3-12.

The treatment method according to any one of Items 3-1 to 3-11, wherein the aqueous liquid preparation is an ophthalmic solution.

Item 4-1.

A method for treating dry eye, comprising administering an aqueous liquid preparation comprising arbekacin and/or a salt thereof and at least one water-soluble polymer to a subject in need thereof, the water-soluble polymer comprising at least one water-soluble polymer selected from the group consisting of hydroxypropyl methylcellulose, hydroxyethylcellulose, methylcellulose, and polyvinylpyrrolidone.

Item 4-2.

A method for increasing the viscosity of the aqueous liquid preparation comprising a water-soluble polymer on the ocular surface, the method comprising administering an aqueous liquid preparation comprising arbekacin and/or a salt thereof and at least one water-soluble polymer to a subject in need thereof, and the water-soluble polymer comprising hydroxypropyl methylcellulose.

Item 4-3.

A method for enhancing adhesion to mucin, comprising administering an aqueous liquid preparation comprising arbekacin and/or a salt thereof and at least one water-soluble polymer to a subject in need thereof, the water-soluble polymer comprising hydroxypropyl methylcellulose.

Item 4-4.

A tear film stabilization method comprising administering an aqueous liquid preparation comprising arbekacin and/or a salt thereof and at least one water-soluble polymer to a subject in need thereof, the water-soluble polymer comprising hydroxypropyl methylcellulose.

Item 4-5.

A method for treating dry eye, comprising administering an aqueous liquid preparation comprising arbekacin and/or a salt thereof and at least one water-soluble polymer to a subject in need thereof, the water-soluble polymer comprising hydroxypropyl methylcellulose.

Item 4-6.

The method according to any one of Items 4-1 to 4-5, wherein the total concentration of the arbekacin and/or a salt thereof in the aqueous liquid preparation is about 0.05 w/v % to about 5.0 w/v %.

Item 4-7.

The method according to any one of Items 4-1 to 4-6, wherein the concentration of the water-soluble polymer in the aqueous liquid preparation is about 0.05 w/v % to about 8.8 w/v %.

Item 4-8.

The method according to any one of Items 4-1 to 4-7, wherein the mass ratio of the total content of the arbekacin and/or a salt thereof to the content of the water-soluble polymer in the aqueous liquid preparation is in the range of about 1:0.04 to about 1:70.

Item 4-9.

The method according to any one of Items 4-1 to 4-8, wherein the aqueous liquid preparation has a pH of about 5.0 to about 8.0.

Item 4-10.

The method according to any one of Items 4-1 to 4-9, wherein the aqueous liquid preparation has a viscosity of about 5 to about 50 mPa·s.

Item 4-11.

A method for treating dry eye, comprising administering an aqueous liquid preparation comprising arbekacin and/or a salt thereof and at least one water-soluble polymer to a subject in need thereof, wherein
- the water-soluble polymer comprises hydroxypropyl methylcellulose;
- the total concentration of the arbekacin and/or a salt thereof is about 0.1 w/v % to about 3.0 w/v %;
- the concentration of the hydroxypropyl methylcellulose is about 0.3 w/v % to about 2.0 w/v %;
- the mass ratio of the total content of the arbekacin and/or a salt thereof to the content of the hydroxypropyl methylcellulose is in the range of about 1:0.04 to about 1:70;
- the aqueous liquid preparation has a pH of about 5.0 to about 8.0; and
- the aqueous liquid preparation has a viscosity of about 5 to about 50 mPa·s.

Item 4-12.

The method according to any one of Items 4-1 to 4-11, wherein the aqueous liquid preparation is an aqueous liquid preparation wherein $$[C - (A + B)] > 0$$

wherein
- A: viscosity increase value (mPa·s) achieved by arbekacin;
- B: viscosity increase value (mPa·s) achieved by the water-soluble polymer; and
- C: viscosity increase value (mPa·s) achieved by arbekacin and the water-soluble polymer; and
- Viscosity increase value (mPa·s)=$(\eta_1-\eta_2)-\eta_3$ wherein
  - $\eta_1$: viscosity of a mixture of a solution (1 mL) containing arbekacin and/or a water-soluble polymer at the concentration in the aqueous liquid preparation and a 6 w/v % mucin solution (1 mL);
  - $\eta_2$: viscosity of a mixture of a solution containing arbekacin and/or a water-soluble polymer at the concentration in the aqueous liquid preparation and a 0.1M phosphate buffer (1 mL); and
  - $\eta_3$: viscosity of a mixture of a 0.1M phosphate buffer (1 mL) and a 6 w/v % mucin solution (1 mL).

Item 4-13.

The method according to any one of Items 4-1 to 4-12, wherein the aqueous liquid preparation has a decrease percentage in the release rate of arbekacin and/or a salt thereof of 5% or more.

Item 4-14.

The method according to any one of Items 4-1 to 4-13, wherein the aqueous liquid preparation is an ophthalmic solution.

Advantageous Effects of Invention

The adhesion of the aqueous liquid preparation to mucin can be enhanced. Further, transferability of an aqueous liquid preparation to the conjunctiva can be improved.

BRIEF DESCRIPTION OF DRAWINGS

FIG. 1 is a release profile of each sample in the dialysis membrane test ((a): samples 20 to 23 (system comprising 1% of arbekacin, 1% of HPMC, and 1% of mucin), (b): samples 24 and 25 (system comprising 3% of arbekacin, 1.5% of HPMC, and 1% of mucin), and (c) samples 26 and 27 (system comprising 0.5% of arbekacin, 1.5% of HPMC, and 1% of mucin)).

DESCRIPTION OF EMBODIMENTS

Embodiments included in the present disclosure are described in more detail below.

1. Definitions

The terms used herein should be understood as being used in the meaning that is commonly used in the art, unless otherwise specified. Accordingly, unless otherwise defined, all technical and scientific terms used herein have the same meaning as commonly understood by one of ordinary skill in the art to which this invention pertains. In the event of a contradiction, the present specification (including the definitions) takes precedence.

As used herein, the "aqueous liquid preparation" is a preparation that contains water as a base and that is in the form of a liquid.

In present specification, the "water-soluble polymer" refers to a polymer that is soluble in water.

In the present specification, the term "arbekacin" refers to 3-amino-3-deoxy-α-D-glucopyranosyl-(1→6)-[2,6-diamino-2,3,4,6-tetradeoxy-α-D-erythro-hexopyranosyl-(1→4)]-1-N-[(2S)-4-amino-2-hydroxybutanoyl]-2-deoxy-D-streptamine. "Arbekacin" is a compound known as an aminoglycoside antibiotic and has potent antibacterial activity against methicillin-resistant *Staphylococcus aureus* (MRSA). Arbekacin is also described in JPS56-051499A and JPS58-134099A. Further, arbekacin is listed in the monograph of the Japanese Pharmacopoeia, 18th edition. In present specification, the concentration and amount of arbekacin and/or a salt thereof are a concentration and an amount in terms of arbekacin, unless otherwise specified.

In the present specification, "hydroxypropyl methylcellulose" is a type of cellulose polymer. Hydroxypropyl methylcellulose refers to a methyl and hydroxypropyl mixed ether of cellulose. Hydroxypropyl methylcellulose may be referred to as hypromellose. Hydroxypropyl methylcellulose is sometimes abbreviated as HPMC.

In the present specification, "hydroxyethylcellulose" is a type of cellulose polymer. Hydroxyethylcellulose refers to partially O-(2-hydroxyethylated) cellulose. Hydroxyethylcellulose is sometimes abbreviated as HEC.

In the present specification, "methylcellulose" is a type of cellulose polymer. Methylcellulose refers to methyl ether of cellulose. Methylcellulose is sometimes abbreviated as MC.

In the present specification, "polyvinylpyrrolidone" is a type of polyvinyl polymer. "Polyvinylpyrrolidone" refers to a linear polymer of 1-vinyl-2-pyrrolidone. Polyvinylpyrrolidone may be referred to as povidone or polyvidone. Polyvinylpyrrolidone is sometimes abbreviated as PVP.

In the present specification, the "viscosity" of the aqueous liquid preparation is measured according to "2.1.3. Cone-flat plate-type rotational viscometer (cone-plate type viscometer)" of "2. Method II, Viscosity measurement by rotational viscometer" of "2.53 Viscosity Determination" in the General Test Method of the Japanese Pharmacopoeia, 18th edition (30° C.±0.1° C., preheat time: 0 s, rotational speed: 100 rpm, cone-plate rotational viscometer, cone rotor used: 3°×R17.65, measurement time: 90 s). Specifically, the viscosity of the aqueous liquid preparation is measured using a viscometer TVE-25 type (model: TVE-25L) produced by Toki Sangyo Co., Ltd.

In the present specification, "viscosity increase value" refers to a value obtained by subtracting the viscosity of arbekacin and/or a water-soluble polymer solution and the viscosity of a mucin solution from the viscosity of a mixture of arbekacin and/or a water-soluble solution and a mucin solution. More specifically, the viscosity increase value refers to a value obtained according to the following calculation formula (Non-patent Literature (NPL) 2):

$$\text{Viscosity increase value (mPa·s)} = (\eta_1 - \eta_2) - \eta_3$$

wherein
 $\eta_1$: viscosity of a mixture of a solution (1 mL) containing arbekacin and/or a water-soluble polymer at the concentration in the aqueous liquid preparation and a 6 w/v % mucin solution (1 mL);
 $\eta_2$: viscosity of a mixture of a solution (1 mL) containing arbekacin and/or a water-soluble polymer at the concentration in the aqueous liquid preparation and a 0.1M phosphate buffer (1 mL); and
 $\eta_3$: viscosity of a mixture of a 0.1M phosphate buffer (1 mL) and a 6 w/v % mucin solution (1 mL).

The viscosity increase value achieved by arbekacin is obtained according to the following calculation formula:

Viscosity increase value achieved by arbekacin (mPa·s)= $(\eta_1 - \eta_2) - \eta_3$ wherein
 $\eta_1$: viscosity of a mixture of a solution (1 mL) containing arbekacin at the concentration in the aqueous liquid preparation and a 6 w/v % mucin solution (1 mL);
 $\eta_2$: viscosity of a mixture of a solution (1 mL) containing arbekacin at the concentration in the aqueous liquid preparation and a 0.1M phosphate buffer (1 mL); and
 $\eta_3$: viscosity of a mixture of a 0.1M phosphate buffer (1 mL) and a 6 w/v % mucin solution (1 mL).

The viscosity increase value achieved by a water-soluble polymer is obtained according to the following calculation formula:

$$\text{Viscosity increase value (mPa·s) achieved by a water-soluble polymer} = (\eta_1 - \eta_2) - \eta_3$$

wherein
 $\eta_1$: viscosity of a mixture of a solution (1 mL) containing a water-soluble polymer at the concentration in the aqueous liquid preparation and a 6 w/v % mucin solution (1 mL);
 $\eta_2$: viscosity of a mixture of a solution (1 mL) containing a water-soluble polymer at the concentration in the aqueous liquid preparation and a 0.1M phosphate buffer (1 mL); and
 $\eta_3$: viscosity of a mixture of a 0.1M phosphate buffer (1 mL) and a 6 w/v % mucin solution (1 mL).

The viscosity increase value achieved by arbekacin and a water-soluble polymer is obtained according to the following calculation formula:

$$\text{Viscosity increase value (mPa·s) achieved by arbekacin and a water-soluble polymer} = (\eta_1 - \eta_2) - \eta_3$$

wherein
 $\eta_1$: viscosity of a mixture of a solution (1 mL) containing arbekacin and a water-soluble polymer at the concentration in the aqueous liquid preparation and a 6 w/v % mucin solution (1 mL);
 $\eta_2$: viscosity of a mixture of a solution (1 mL) containing arbekacin and a water-soluble polymer at the concentration in the aqueous liquid preparation and a 0.1M phosphate buffer (1 mL); and
 $\eta_3$: viscosity of a mixture of a 0.1M phosphate buffer (1 mL) and a 6 w/v % mucin solution (1 mL)

In the present specification, "thicken(ing)" refers to increasing the viscosity of an aqueous arbekacin liquid preparation containing a water-soluble polymer by an interaction of the liquid preparation with mucin.

In the present specification, the "decrease percentage of release rate of arbekacin and/or a salt thereof (%)" is an indicator of the adhesion of arbekacin to mucin. The higher the decrease percentage, the higher the adhesion. "The decrease percentage of the release rate of arbekacin and/or a salt thereof (%)" is calculated based on the results of the in vitro dialysis membrane test described below.

In Vitro Dialysis Membrane Test
1) 500 μL of a sample (containing arbekacin and/or a salt thereof) is sealed in a 2-mL volume glass container. The opening is covered with a dialysis membrane, and the surrounding area was fixed (the inside the glass container is the donor side).
2) The sample-containing container thus obtained in 1) is attached to a beaker (outer liquid side) filled with PBS (15 mL) at a constant height from the bottom of the beaker. The liquid in the beaker is stirred with a stirrer.
3) 1 mL of liquid was sampled from the outer liquid side at any time between 15 and 240 minutes after the start of stirring and used as a sampling solution. The sampling solution is appropriately diluted and measured by liquid chromatography under the following conditions.

Detector: charged aerosol detector
Column: a commercially available product comprising a stainless steel tube having an inner diameter of 4.6 mm and a length of 250 mm, and filled with 5 μm octylsilylated silica gel for liquid chromatography.
Column temperature: constant temperature around 30° C.
Mobile phase: gradients with a 5 mM aqueous heptafluorobutyric acid solution and a 5 mM heptafluorobutyric acid acetonitrile solution
Flow rate: 1.4 mL per minute Percentage of drug remaining in a donor relative to the theoretical total amount (%)=100−(Cumulative amount of arbekacin released into the outer liquid by the time of sampling (μg)/Theoretical total amount of arbekacin on the donor side (μg)×100).

Release rate (%/min): absolute value of the slope of the approximate line obtained by the least-squares method when the percentage of remaining drug (%) and the sampling time (min) are respectively plotted on the y-axis and the x-axis for each sampling solution.

Decrease percentage in release rate (%): 100−(release rate of sample/release rate of an arbekacin solution alone×100)

The "arbekacin solution" in the calculation formula for the decrease percentage in the release rate (%) is an aqueous solution of arbekacin or a salt thereof, wherein the solution contains arbekacin in the same amount as the arbekacin contained in the sample. The "arbekacin solution" is a solution obtained by dissolving the same compound as arbekacin and/or a salt thereof contained in the sample in water in the same amount as for the sample. For example, if the sample contains 1 w/v % arbekacin sulfate in terms of arbekacin, the "arbekacin solution" is an aqueous solution of 1 w/v % arbekacin sulfate in terms of arbekacin.

In the present specification, "mucin adhesion" or "adhesion to mucin" refers to the ability to reversibly bind a water-soluble polymer, arbekacin, and mucin by their interaction with each other in an aqueous solution when an aqueous arbekacin liquid preparation containing a water-soluble polymer is mixed with mucin.

In the present specification, "improving transferability of arbekacin to the conjunctiva" means that the $C_{max}$ of the arbekacin concentration in the conjunctiva when an aqueous liquid preparation of arbekacin containing a water-soluble polymer is administered is higher than the $C_{max}$ of the arbekacin concentration in the conjunctiva when an aqueous liquid preparation of arbekacin not containing a water-soluble polymer is administered. $C_{max}$ refers to the highest drug concentration at the target site after drug administration.

In the present specification, "bacterial external ocular infection" refers to a disease caused by a bacterial infection of the external eye area. The term "external ocular" refers to an organ located around the eyeball. Examples include the conjunctiva, cornea, eyelids, lacrimal glands, and meibomian glands.

In the present specification, "bacterial keratoconjunctivitis" refers to a disease in which inflammation is caused by a bacterial infection of the cornea or conjunctiva. "Bacterial keratitis" refers to a disease in which inflammation is caused by a bacterial infection of the cornea. "Bacterial conjunctivitis" refers to a disease in which inflammation is caused by a bacterial infection of the conjunctiva.

In the present specification, "dry eye" refers to a condition diagnosed as "dry eye" according to clinical diagnostic criteria. More specifically, dry eye is "a multifactorial ocular surface disease characterized by a collapse in the health of the tear film with some subjective eye symptoms, and the instability and hyperosmolarity of the tear film, inflammation and damage of the ocular surface, and sensory neuropathy play an etiological role" (Non-patent Literature (NPL) 3). "Dry eye" is sometimes referred to as "dry keratoconjunctivitis." In the present specification, "treatment" means the amelioration, alleviation, mitigation, or slowing down of the progression, of a disease or symptom.

In the present specification, the term "tear film" refers to a film covering the surface of the eye, the film consisting of three layers: a lipid layer (oil layer), a water layer, and a mucin layer. If the water layer and the mucin layer are considered as one liquid film in a mixture of the water layer and the mucin layer, the tear film refers to a film covering the surface of the eye and consisting of two layers: a liquid layer composed of a mixture of water and mucin; and an oil layer (Non-Patent Literature (NPL) 3).

In the present specification, "tear film stabilization" means that the tear film is stably maintained on the surface of the eye. The tear film break-up time (BUT) refers to the time from the formation to the breakup of the tear film. When the tear film becomes unstable, the BUT tends to shorten. For example, the "tear film stabilization" refers to prolongation of the BUT.

In the present specification, "about" refers to a range of ±10% from the numerical value that is described subsequent to "about", unless noted otherwise.

2. Aqueous Liquid Preparation

The aqueous liquid preparation included in the present disclosure contains arbekacin and/or a salt thereof and at least one water-soluble polymer selected from the group consisting of hydroxypropyl methylcellulose, hydroxyethylcellulose, methylcellulose, and polyvinylpyrrolidone. In the present specification, this aqueous liquid preparation is sometimes referred to as the "aqueous liquid preparation of the present disclosure."

The salt of arbekacin is not limited as long as it is pharmacologically acceptable. Examples include organic acid salts or inorganic acid salts. Examples of organic acid salts include tartrate and acetate. Examples of inorganic acid salts include sulfate and hydrochloride. Arbekacin or a salt thereof may also be in the form of solvates, such as hydrates. Among arbekacin or salts thereof, arbekacin sulfate is preferably used because it is commercially available as a pharmaceutical product and its safety has been established.

In the aqueous liquid preparation of the present disclosure, either arbekacin or one of its salts may be used alone, or these may be used in combination.

The total concentration of arbekacin and/or a salt thereof in the aqueous liquid preparation of the present disclosure can be, for example, about 0.05 to about 5.0 w/v % in terms of arbekacin. The upper or lower limit of the range can be, for example, about 0.1, about 0.2, about 0.3, about 0.4, about 0.5, about 0.6, about 0.7, about 0.8, about 0.9, about 1.0, about 1.5, about 2.0, about 2.5, about 3.0, about 3.5, about 4.0 or about 4.5 w/v %. For example, the range can preferably be about 0.1 to about 3.0 w/v %.

The water-soluble polymer used in the composition of the present disclosure includes hydroxypropyl methylcellulose, hydroxyethyl cellulose, methyl cellulose, and polyvinyl pyrrolidone. These four water-soluble polymers are sometimes collectively referred to as the water-soluble polymer of the present disclosure. Of these, hydroxypropyl methylcellulose is particularly preferred because it can easily maintain the viscosity over time. Such water-soluble polymers can be used alone or in a combination of two or more. The composition of the present disclosure may contain water-soluble polymers other than the water-soluble polymer of the present disclosure as long as the effect is not impaired.

The degree-of-substitution type of hydroxypropyl methylcellulose is defined by the methoxy group content and hydroxypropoxy group content (Japanese Pharmacopoeia, 18th edition). The degree-of-substitution type 1828 refers to hydroxypropyl methylcellulose with a methoxy group content of 16.5 mass % (the lower limit) or more and 20.0 mass % (the upper limit) or less, and with a hydroxypropoxy group content of 23.0 mass % (the lower limit) or more and 32.0 mass % (the upper limit) or less. The degree-of-substitution type 2208 refers to hydroxypropyl methylcellulose with a methoxy group content of 19.0 mass % (the lower limit) or more and 24.0 mass % (the upper limit) or less, and with a hydroxypropoxy group content of 4.0 mass % (the lower limit) or more and 12.0 mass % (the upper limit) or less. The degree-of-substitution type 2906 refers to hydroxypropyl methylcellulose with a methoxy group content of 27.0 mass % (the lower limit) or more and 30.0 mass % (the upper limit) or less and a hydroxypropoxy group content of 4.0 mass % (the lower limit) or more and 7.5 mass % (the upper limit) or less. The degree-of-substitution type 2910 refers to hydroxypropyl methylcellulose with a methoxy group content of 28.0 mass % (the lower limit) or more and 30.0 mass % (the upper limit) or less, and with a hydroxypropoxy group content of 7.0 mass % (the lower limit) or more and 12.0 mass % (the upper limit) or less.

The degree-of-substitution type of hydroxypropyl methylcellulose is not particularly limited and may be 1828, 2208, 2906, or 2910; and is preferably, for example, 2208 or 2910.

The molecular weight of hydroxypropyl methylcellulose is not particularly limited. The weight average molecular weight is, for example, 10000 to 500000, preferably 50000 and 500000, and more preferably 50000 to 300000. For example, the weight average molecular weight can be determined by gel filtration chromatography (GPC) using polystyrene as a standard substance.

The concentration of hydroxypropyl methylcellulose in the aqueous liquid preparation of the present disclosure can be, for example, about 0.2 to about 3.5 w/v %, preferably about 0.3 to about 2.0 w/v %, more preferably about 0.3 to about 1.5 w/v %, even more preferably about 0.8 to about 1.5 w/v %, and particularly preferably about 0.8 to about 1.4 w/v %.

The molar degree of substitution of hydroxyethoxy groups (average number of moles of hydroxyethoxy groups added per anhydrous glucose unit) in hydroxyethyl cellulose is not particularly limited and can be, for example, about 1.5 to 3.0, and more preferably about 2.5.

The molecular weight of hydroxyethyl cellulose is not particularly limited. For example, the weight average molecular weight is 10000 to 1000000, preferably 100000 to 1000000, and more preferably 600000 to 800000.

The concentration of hydroxyethylcellulose in the aqueous liquid preparation of the present disclosure can be, for example, about 0.05 to about 1 w/v %; and, for example, may be about 0.08 to about 0.6 w/v %, or may be about 0.09 to about 0.4 w/v %, or may be about 0.2 to about 0.4 w/v %.

The degree of substitution (average number of hydroxyl groups substituted with methoxy groups per anhydrous glucose unit) of methylcellulose is not particularly limited and can be, for example, about 1.5 to 3.0, and preferably about 1.8.

The molecular weight of methylcellulose is not particularly limited. For example, the weight average molecular weight is 10000 to 500000, preferably 100000 to 500000, and more preferably 300000 to 500000.

The concentration of methylcellulose in the aqueous liquid preparation of the present disclosure can be, for example, about 0.1 to about 1.8 w/v %. For example, the concentration may be about 0.15 to about 1.0 w/v %, may be about 0.15 to about 0.75 w/v %, may be about 0.4 to about 0.75 w/v %, and may be about 0.4 to about 0.7 w/v %.

The molecular weight of polyvinylpyrrolidone is not particularly limited. For example, the weight average molecular weight is 2000 to 1500000, preferably 40000 to 1500000, more preferably 1000000 to 1500000.

The concentration of polyvinylpyrrolidone in aqueous liquid preparation of the present disclosure can be, for example, about 0.5 to about 8.8 w/v %. For example, the concentration of polyvinylpyrrolidone may be about 0.75 to about 5.0 w/v %, may be about 0.75 to about 3.8 w/v %, may be about 2.0 to about 3.8 w/v %, and may be about 2.0 to about 3.5 w/v %.

The composition of the present disclosure may contain water-soluble polymers other than the water-soluble polymer of the present disclosure as long as the effect is not impaired. Examples of other water-soluble polymers include cellulose polymers and synthetic polymers other than the water-soluble polymer of the present disclosure.

More specifically, examples of cellulose polymers include non-ionic (nonionic) cellulose polymers and ionic cellulose polymers. Examples of non-ionic cellulose polymers include ethyl cellulose, hydroxymethyl cellulose, hydroxypropyl cellulose, and hydroxyethylmethyl cellulose. Examples of ionic cellulose polymers include carboxymethyl cellulose, hydroxypropyl methylcellulose acetate succinate, hydroxypropyl methylcellulose phthalate, carboxymethyl ethyl cellulose, and cellulose acetate phthalate.

Examples of the synthetic polymers include carboxyvinyl polymers, polyacrylic acid, and polyvinyl alcohol.

When the composition of the present disclosure further contains one or more such other water-soluble polymers, the water-soluble polymer of the present disclosure preferably accounts for at least 50 mass %, more preferably 55, 60, 65, 70, 75, 80, 85, 90, or 95 mass %, and particularly preferably 100 mass %, of the water-soluble polymers contained in the composition.

The total concentration of the water-soluble polymer of the present disclosure in the aqueous liquid preparation of the present disclosure can be, for example, about 0.05 w/v % to about 8.8 w/v %. The upper limit or lower limit of the range can be, for example, about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, or about 8.7 w/v %. The range of the total concentration may be, for example, about 0.1 to about 7 w/v %, or may be about 0.2 to about 6 w/v %, or may be about 0.3 to about 5 w/v %.

The total concentration of the water-soluble polymers in the aqueous liquid preparation of the present disclosure can be, for example, about 0.05 w/v % to about 8.8 w/v %. The upper limit or lower limit of the range can be, for example, about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, or about 8.7 w/v %. The range of the total concentration may be, for example, about 0.1 to about 7 w/v %, or may be about 0.2 to about 6 w/v %, or may be about 0.3 to about 5 w/v %.

In the aqueous liquid preparation of the present disclosure, the ratio of the water-soluble polymer of the present disclosure to arbekacin and/or a salt thereof is not particularly limited as long as the effect is not impaired. For example, the mass ratio of the total content of arbekacin and/or a salt thereof in terms of arbekacin to the content of the water-soluble polymer of the present disclosure (total content of arbekacin and/or a salt thereof in terms of arbekacin: content of the water-soluble polymer of the present disclosure) can be in the range of about 1:0.01 to about 1:180 parts by mass. The upper limit or lower limit of the mass ratio range (about 0.01 to about 180) can be, for example, about 0.02, about 0.03, about 0.04, about 0.05, about 0.1, about 0.15, about 0.2, about 0.25, about 0.3, about 0.35, about 0.4, about 0.45, about 0.5, about 0.6, about 0.7, about 0.8, about 0.9, about 1, about 1.5, about 2, about 2.5, about 3, about 3.5, about 4, about 4.5, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 55, about 60, about 65, about 70, about 75, about 80, about 85, about 90, about 95, about 100, about 110, about 120, about 130, about 140, about 150, about 160, or about 170. Thus, the mass ratio may be, for example, in the range of about 1:0.01 to about 1:110 parts by mass, may be in the range of about 1:0.04 to about 1:70 parts by mass, may be in the range of about 1:0.1 to about 1:20 parts by mass, or may be in the range of about 1:0.25 to about 1:14 parts by mass.

Further, in the aqueous liquid preparation of the present disclosure, the ratio of the water-soluble polymer (s) to arbekacin and/or a salt thereof is not particularly limited as long as the effect is not impaired. For example, the mass ratio of the total content of arbekacin and/or a salt thereof in terms of arbekacin to the water-soluble polymer content can be in the range of about 1:0.01 to about 1:180 parts by mass. The upper limit or lower limit of the mass ratio range (about 0.01 to about 180) can be, for example, about 0.02, about 0.03, about 0.04, about 0.05, about 0.1, about 0.15, about 0.2, about 0.25, about 0.3, about 0.35, about 0.4, about 0.45, about 0.5, about 0.6, about 0.7, about 0.8, about 0.9, about 1, about 1.5, about 2, about 2.5, about 3, about 3.5, about 4, about 4.5, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 55, about 60, about 65, about 70, about 75, about 80, about 85, about 90, about 95, about 100, about 110, about 120, about 130, about 140, about 150, about 160, or about 170. Thus, the mass ratio may be, for example, in the range of about 1:0.01 to about 1:110 parts by mass, may be in the range of about 1:0.04 to about 1:70 parts by mass, may be in the range of about 1:0.1 to about 1:20 parts by mass, or may be in the range of about 1:0.25 to about 1:14 parts by mass.

The aqueous liquid preparation of the present disclosure may contain additives, such as buffers, isotonic agents, surfactants, antiseptics or preservatives, cooling agents, stabilizers, and pH adjusters.

The aqueous liquid preparation of the present disclosure may contain bromfenac, diclofenac, tromethamine, flurbiprofen, ketorolac, or a pharmacologically acceptable salt thereof.

The buffers are not particularly limited as long as they are pharmacologically acceptable. Examples include borate buffers, citrate buffers, phosphate buffers, Tris buffers, tartrate buffers, acetate buffers, and amino acid buffers. Such buffers can be used alone or in a combination of two or more.

Specific examples of borate buffers include boric acid and/or salts thereof. The boric acid is not particularly limited as long as it is pharmaceutically acceptable. Examples include orthoboric acid, metaboric acid, and tetraboric acid. Among these, orthoboric acid and tetraboric acid are preferred. Such boric acid can be used alone or in a combination of two or more. The boric acid salts are not particularly limited as long as they are pharmaceutically acceptable. Examples include alkali metal salts such as sodium salts and potassium salts; alkaline earth metal salts such as calcium salts and magnesium salts; aluminium salts; and organic amine salts such as salts of triethylamine, triethanolamine, morpholine, piperazine, and pyrrolidine. Boric acids/or salts thereof may also be in the form of hydrates, such as borax.

As the borate buffer, boric acid and salts thereof may be selected and used alone or in a combination of two or more. Among the boric acid and salts thereof, at least one member selected from boric acid and borax, and more preferably at least one of orthoboric acid and borax can be preferably used.

Specific examples of citrate buffers include citric acid and/or salts thereof. The citric acid salts are not particularly limited as long as they are pharmaceutically acceptable. Examples include alkali metal salts such as sodium salts and potassium salts; and alkaline earth metal salts such as calcium salts and magnesium salts. The citric acid salts may also be in the form of solvates, such as hydrates. As the citrate buffer, citric acid and salts thereof may be selected and used alone or in a combination of two or more. Among the citric acid and salts thereof, the citrate buffer is preferably a citric acid salt, more preferably an alkali metal salt of citric acid, and particularly preferably sodium citrate.

Specific examples of phosphate buffers include phosphoric acid and/or salts thereof. The phosphoric acid salts are not particularly limited as long as they are pharmaceutically acceptable. Examples of phosphoric acid salts include di-alkali metal hydrogen phosphates such as disodium hydrogen phosphate and dipotassium hydrogen phosphate; alkali metal dihydrogen phosphates such as sodium dihydrogen phosphate and potassium dihydrogen phosphate; and tri-alkali metal phosphates such as trisodium phosphate and tripotassium phosphate. The phosphoric acid salts may also be in the form of solvates, such as hydrates. For example, disodium hydrogen phosphate can be in the form of dodecahydrate. Sodium dihydrogen phosphate can be in the form of, for example, dihydrate. As the phosphate buffer, phosphoric acid and salts thereof may be selected and used alone or in a combination of two or more. Among the phosphoric acid and salts thereof, the phosphate buffer is preferably a phosphoric acid salt, more preferably at least one member selected from di-alkali metal hydrogen phosphates and alkali metal dihydrogen phosphates, and particularly preferably at least one of disodium hydrogen phosphate and sodium dihydrogen phosphate.

Specific examples of Tris buffers include trometamol and/or salts thereof. The trometamol salts are not particularly limited as long as they are pharmaceutically acceptable. Examples include organic acid salts such as acetates; and inorganic acid salts such as hydrochlorides and sulfonates. As the Tris buffer, trometamol and salts thereof may be selected and used alone or in a combination of two or more. Among the trometamol and salts thereof, trometamol is preferred.

Specific examples of tartrate buffers include tartaric acid and/or salts thereof. The tartaric acid salts are not particularly limited as long as they are pharmaceutically acceptable. Examples include alkali metal salts such as sodium and potassium salts; and alkaline earth metal salts such as calcium salts and magnesium salts. The tartaric acid salts may also be in the form of solvates, such as hydrates. As the tartrate buffer, tartaric acid and salts thereof may be selected and used alone or in a combination of two or more.

Specific examples of acetate buffers include acetic acid and/or salts thereof. The acetic acid salts are not particularly limited as long as they are pharmaceutically acceptable. Examples include alkali metal salts such as sodium salts and potassium salts; alkaline earth metal salts such as calcium salts and magnesium salts; and ammonium salts. The acetic acid salts may also be in the form of solvates, such as hydrates. As the acetate buffer, acetic acid and salts thereof may be selected and used alone or in a combination of two or more.

Specific examples of amino acid buffers include acidic amino acids and/or salts thereof. Specific examples of acidic amino acids include aspartic acid and glutamic acid. The acidic amino salts are not particularly limited as long as they are pharmaceutically acceptable. Examples include alkali metal salts such as sodium salts and potassium salts. As the amino acid buffer, acidic amino acids and salts thereof may be selected and used alone or in a combination of two or more.

The concentration of the buffer in the aqueous liquid preparation of the present disclosure may be appropriately set within the range that the aqueous liquid preparation has the desired buffering capacity. For example, the concentration of the buffer can be in the range of about 0.01 to 3.0 w/v %.

The isotonic agents are not particularly limited as long as they are pharmaceutically acceptable. Examples include polyhydric alcohols such as glycerin, propylene glycol, butylene glycol, and polyethylene glycol; metal salts such as sodium chloride, potassium chloride, calcium chloride, magnesium chloride, sodium acetate, potassium acetate, sodium hydrogen sulphite, sodium hydrogen carbonate, sodium carbonate, disodium hydrogen phosphate, and sodium dihydrogen phosphate. Such isotonic agents may be used alone or in a combination of two or more.

The surfactants are not particularly limited as long as they are pharmaceutically acceptable. Examples include nonionic surfactants such as tyloxapol, polyoxyethylene hardened castor oil, polyoxyethylene polyoxypropylene block copolymers, polyoxyethylene sorbitan fatty acid esters, and octoxynol; amphoteric surfactants such as alkyl diaminoethyl glycine and betaine lauryl dimethylaminoacetate; anionic surfactants such as alkyl sulfates, N-acyltaurates, polyoxyethylene alkyl ether phosphates, and polyoxyethylene alkyl ether sulfates; and cationic surfactants such as alkylpyridinium salts and alkylamine salts. Such surfactants may be used alone or in a combination of two or more.

The antiseptics or preservatives are not particularly limited as long as they are pharmaceutically acceptable. Examples include sorbic acid or salts thereof, benzoic acid or salts thereof, methyl paraoxybenzoate, ethyl paraoxybenzoate, propyl paraoxybenzoate, chlorobutanol, benzalkonium chloride, chlorhexidine hydrochloride, chlorhexidine gluconate, chlorhexidine acetate, dehydroacetic acid or salts thereof, benzethonium chloride, benzyl alcohol, zinc chloride, zinc sulfate, silver nitrate, polyhexanide, alkyl diaminoethylglycine hydrochloride, para-chloro-meta-xylenol, chlorocresol, phenethyl alcohol, polydronium chloride, thimerosal, dibutylhydroxytoluene, and povidone iodine (PVPI). Such antiseptics or preservatives may be used alone or in a combination of two or more.

The cooling agents are not particularly restricted as long as they are pharmaceutically acceptable. Examples include 1-menthol, borneol, camphor, and eucalyptus oil. Such cooling agents may be used alone or in a combination of two or more.

The stabilizers are not particularly limited as long as they are pharmaceutically acceptable. Examples include chelating agents such as edetic acid, citric acid, succinic acid, ascorbic acid, trihydroxymethylaminomethane, nitrilotriacetic acid, 1-hydroxyethane-1,1-diphosphonic acid, polyphosphoric acid, metaphosphoric acid, hexamethaphosphoric acid, and salts thereof; and sodium thiosulfate, sulphites, monoethanolamine, cyclodextrin, dextran, ascorbic acid, taurine, tocopherol, and dibutylhydroxytoluene. The salts are not particularly limited as long as they are pharmaceutically acceptable. Examples include alkali metal salts such as sodium salts and potassium salts. Such stabilizers may be used alone or in a combination of two or more.

The pH adjusters are not particularly limited as long as they are pharmaceutically acceptable. Examples include acids such as hydrochloric acid, acetic acid, boric acid, aminoethylsulfonic acid, and epsilon-aminocaproic acid; and alkalis such as sodium hydroxide, potassium hydroxide, borax, triethanolamine, monoethanolamine, sodium hydrogen carbonate, and sodium carbonate. Such pH adjusters may be used alone or in a combination of two or more.

The concentration of these additives may be appropriately set according to the type of additive used and the properties etc. to be imparted to the aqueous liquid preparation.

The pH of the aqueous liquid preparation of the present disclosure is not particularly limited as long as it is pharmaceutically acceptable, and is about 5.0 to about 8.0. For example, the pH may be about 5.4 to about 7.5, about 5.4 to about 7.0, or about 5.4 to about 6.0.

The viscosity of the aqueous liquid preparation of the present disclosure is not particularly limited, and is about 5.0 to about 100 mPa·s. For example, the viscosity of the aqueous liquid preparation may be about 5 to about 50 mPa·s, about 10 to about 35 mPa·s, or about 20 to about 35 mPa·s.

The osmotic pressure of the aqueous liquid preparation is the value measured according to the method specified in "2.47 Osmolarity Determination" in the General Test Method of Japanese Pharmacopoeia 18th edition. The osmotic pressure of the aqueous liquid preparation of the present disclosure is not particularly limited as long as the aqueous liquid preparation can be applied to the intended use. For example, when the aqueous liquid preparation is applied to the ocular mucosa, the osmotic pressure is about 243 to 350 mOsm/kg.

The osmotic pressure ratio of the aqueous liquid preparation indicates the ratio of the osmotic pressure of the aqueous liquid preparation to the osmotic pressure of saline (0.9 w/v % sodium chloride aqueous solution). The osmotic pressure ratio of the aqueous liquid preparation of the present disclosure is not particularly limited as long as the aqueous liquid preparation can be applied to the intended use. For example, when the aqueous liquid preparation is applied to the ocular mucosa, the osmotic pressure ratio is 0.85 to 1.15. The osmotic pressure ratio is preferably 0.9 to 1.1, and more preferably 1.0 in terms of reducing eye irritation.

In the aqueous liquid preparation of the present disclosure, the value obtained by subtracting a viscosity increase value attained by arbekacin and the viscosity increase value attained by a water-soluble polymer from the viscosity increase value attained by arbekacin and a water-soluble polymer is preferably greater than 0. In other words, in the aqueous liquid preparation of the present disclosure, it is preferable that C−(A+B) is greater than 0 (C−(A+B)>0).

A: Viscosity increase value (mPa·s) achieved by arbekacin

B: Viscosity increase value (mPa·s) achieved by a water-soluble polymer

C: Viscosity increase value (mPa·s) achieved by arbekacin+a water-soluble polymer.

For example, C−(A+B) may be greater than about 0.1, about 0.15, about 0.2, about 0.25, about 0.3, about 0.35, about 0.4, about 0.45, about 0.5, about 0.55, about 0.6, or about 0.65. Of these, C−(A+B) is preferably about 0.1, more preferably about 0.3, and even more preferably about 0.5.

The aqueous liquid preparation of the present disclosure preferably has a decrease percentage in the release rate of arbekacin and/or a salt thereof of about 5% or more. For example, the decrease percentage in the release rate of arbekacin and/or a salt thereof may be greater than about 5, about 6, about about 7, about 8, about 9, about 10, about 11, about 12, about 13, about 14, about 15, about 16, about 17, about 18, about 19, about 20, about 21, about 22, about 23, about 24, or about 25%. Of these, the decrease percentage in the release rate is preferably about 5%, more preferably about 15%, and even more preferably about 25%.

The dosage form of the aqueous liquid preparation of the present disclosure is not particularly limited, and can be a solution, suspension, or emulsion. It is preferably a solution.

The aqueous liquid preparation of the present disclosure may be produced according to known preparation methods depending on the dosage form, e.g., using the methods described in the General Rules for Preparations of Japanese Pharmacopoeia 18th edition.

Specifically, for example, the method for producing an aqueous liquid preparation according to the present disclosure comprises incorporating arbekacin and/or a salt thereof and at least one water-soluble polymer selected from the group consisting of hydroxypropyl methylcellulose, hydroxyethyl cellulose, methylcellulose, and polyvinylpyrrolidone in a pharmaceutically acceptable aqueous medium. The "pharmaceutically acceptable aqueous medium" means a pharmaceutically acceptable aqueous medium, e.g., purified water. In the incorporation step, the order of incorporation of components is not particularly limited. The components may be incorporated sequentially in any order or simultaneously.

The aqueous liquid preparation of the present disclosure is prepared into pharmaceutical compositions for various applications, e.g., ophthalmic, dental, otolaryngological, and dermatological applications, and used as a topically administered preparation. The aqueous liquid preparation of the present disclosure can be formed into, for example, a composition for ophthalmic, dental, otolaryngological, or dermatological applications. Preferable examples include an ophthalmic composition.

Examples of the ophthalmic composition include ophthalmic solutions, eye washes, contact lens preparations, and injections. Of these, ophthalmic solutions are preferable.

Arbekacin and/or a salt thereof in the aqueous liquid preparation of the present disclosure produce an antibacterial effect against gram-positive and gram-negative bacteria. Accordingly, the aqueous liquid preparation of the present disclosure can be preferably used in the treatment of bacterial external ocular infection and bacterial keratoconjunctivitis (bacterial conjunctivitis and/or bacterial keratitis), and can be more preferably used for treating bacterial conjunctivitis.

Examples of bacteria causing bacterial external ocular infections include gram-positive and gram-negative bacteria. Examples of gram-positive bacteria that cause bacterial conjunctivitis include *Staphylococcus* spp., (e.g., methicillin-resistant *Staphylococcus aureus*), *Streptococcus pneumoniae*, and *Corynebacterium* spp. Examples of gram-negative bacteria that cause bacterial conjunctivitis include *Haemophilus influenzae, Moraxella* spp., and *Neisseria gonorrhoeae* (Noriko Inada, Clinical Ophthalmology, vol. 75, No. 11, 2021).

Examples of bacteria causing bacterial keratitis include *Streptococcus pneumoniae, Staphylococcus, Pseudomonas*

*aeruginosa*, *Moraxella*, *Serratia*, *Streptococcus*, *Neisseria gonorrhoeae*, anaerobic bacteria, and atypical mycobacteria (Guidelines for Infectious Keratitis Treatment (second edition), Japanese Ophthalmological Society, 2013).

The bacteria causing bacterial external ocular infections and bacterial keratoconjunctivitis may be used alone or in a combination of two or more.

As the bacteria causing bacterial external ocular infections (more specifically, bacterial keratoconjunctivitis), *Staphylococcus* spp., (e.g., methicillin-resistant *Staphylococcus aureus*), *Corynebacterium* spp., *Pseudomonas aeruginosa*, *Haemophilus influenza*, *Streptococcus pneumoniae*, *Moraxella*, *Neisseria gonorrhoeae*, *Serratia*, and *Streptococcus* are preferable; *Staphylococcus* spp., (e.g., methicillin-resistant *Staphylococcus aureus*), *Corynebacterium* spp., *Pseudomonas aeruginosa*, *Haemophilus influenza*, and *Streptococcus pneumoniae* are more preferable; *Staphylococcus* spp. (e.g., methicillin-resistant *Staphylococcus aureus*) are even more preferable; and methicillin-resistant *Staphylococcus aureus* are particularly preferable.

Non-ionic water-soluble polymers, such as hydroxypropyl methylcellulose, methylcellulose, and polyvinylpyrrolidone are known not to have mucin adhesion (Non-patent Literature 4). However, as shown in the Examples below, it was found that in the aqueous liquid preparation of the present disclosure, the combination use of these water-soluble polymers with arbekacin and/or a salt thereof allows for interaction with mucin to increase its viscosity. As the viscosity of the ophthalmic solution is increased, the ophthalmic solution is likely to remain on an ocular surface for a longer period of time, thus improving the transferability of the drug to the target site, such as a cornea or conjunctiva. Further, when the aqueous liquid preparation of the present disclosure is mixed with mucin, the water-soluble polymer, arbekacin, and mucin interact with one another in the aqueous solution. Having an ability of reversibly binding these components contributes to an improvement in transferability. Mucin is classified into secretory mucin and membrane-type mucin, and both of which have a terminal carboxyl group and are negatively charged. Mucins repel each other, and a mucin layer is formed in such a manner that the secretory mucin is spread over the membrane-type mucin expressed on epithelial cells of the cornea and conjunctiva (see Non-patent Literature 5). Both of the secretory mucin and membrane-type mucin are known to contribute to the stabilization of a tear film (Non-patent Literature 6). The aqueous liquid preparation of the present disclosure is more likely to remain in the tear fluid for a longer period of time by the interaction with secretory mucin floating in the aqueous layer of the tear film. Additionally, by the interaction with the membrane-type mucin that is expressed to grow on the surface of epithelial cells in a cornea and conjunctiva, the aqueous liquid preparation of the present disclosure is adhered to the ocular surface, and is more likely to gather near the target site such as a cornea and conjunctiva. Accordingly, when the aqueous liquid preparation of the present disclosure is administered to eyes, excellent transferability of arbekacin to the target site such as a cornea and conjunctiva is achieved by the effect of increasing the viscosity on the ocular surface and adhesion effect on mucin. Since the aqueous liquid preparation of the present disclosure has excellent transferability of arbekacin, it exhibits an excellent effect on the treatment of bacterial external ocular infection (more specifically, bacterial keratoconjunctivitis).

When the viscosity of the mucin layer is increased, the destruction of the tear film on the ocular surface is suppressed, and the BUT is prolonged. Specifically, it has been known that the tear film is stabilized (see Non-patent Literature 6 and 7). By the interaction with mucin, the aqueous liquid preparation of the present disclosure can increase the viscosity as a tear film, and can stabilize the tear film. When the aqueous liquid preparation of the present disclosure is administered to eyes, the tear film is stabilized, which allows the tear film to remain on a cornea for a longer period of time to prevent the exposure of the ocular surface, thus exhibiting an ocular surface-protecting effect. Accordingly, the aqueous liquid preparation of the present disclosure can be suitably used for tear film stabilization.

One of the pathologies of dry eye includes the destabilization of the tear film and shortening of BUT, which may disrupt the protection of the ocular surface and cause superficial punctate keratopathy (SPK). When the aqueous liquid preparation of the present disclosure is administered to eyes, the tear film is stabilized. Accordingly, the BUT is prolonged and the SPK is improved; and the aqueous liquid preparation of the present disclosure can be used for treating dry eye.

The tear film has been known to protect an ocular surface from bacteria, and attention has been focused on the antibacterial activity of mucin (Non-patent Literature 8). When the aqueous liquid preparation of the present disclosure is administered to eyes, the tear film is stabilized, and the tear film thus protects the ocular surface. Accordingly, external enemies such as bacteria are less likely to enter, which enables the tear fluid to more effectively exhibit an inherent antibacterial activity. In addition to this, by the effects of increasing the viscosity and enhancing adhesion, the antibacterial effect of arbekacin is also enhanced. Thus, the aqueous liquid preparation of the present disclosure has an excellent effect on the treatment of bacterial external ocular infection (more specifically, bacterial keratoconjunctivitis).

In dry eye, the protection of an ocular surface by a tear film fails, making it easier for external enemies such as bacteria to enter; additionally, the inherent antibacterial activity of the tear fluid may be reduced. If a person has bacterial conjunctivitis under such conditions, the risk that the causative bacteria will pass through the cornea via the ocular surface is increased, which may then cause bacterial keratitis. Since the aqueous liquid preparation of the present disclosure has a tear film stabilization effect in addition to the effect of the treatment of bacterial external ocular infection by arbekacin, it can be particularly used for the treatment of bacterial external ocular infection with dry eye.

The aqueous liquid preparation of the present disclosure can be administered to, for example, humans and mammals other than humans (e.g., rats, mice, rabbits, cows, pigs, dogs, cats, sheep, monkeys, and the like). Examples of humans to whom the aqueous liquid preparation is administered include patients infected with bacterial keratoconjunctivitis or humans possibly infected with bacterial keratoconjunctivitis, and humans infected with the bacteria mentioned above. More specifically, humans infected or possibly infected with *Staphylococcus* spp., (e.g., methicillin-resistant *Staphylococcus aureus*), *Corynebacterium* spp., *Pseudomonas aeruginosa*, *Haemophilus influenzae*, *Streptococcus pneumoniae*, *Moraxella*, *Neisseria gonorrhoeae*, *Serratia*, or *Streptococcus* spp. are preferable; humans infected or possibly infected with *Staphylococcus* spp., (e.g., methicillin-resistant *Staphylococcus aureus*), *Corynebacterium*, *Pseudomonas aeruginosa*, *Haemophilus influenzae*, or *Streptococcus pneumoniae* are more preferable; humans infected or possibly infected with *Staphylococcus* spp. (for example, methicillin-resistant *Staphylococcus* aureus) are even more preferable; and humans infected or possibly infected with methicillin-resistant *Staphylococcus aureus* are particularly preferable.

Examples of humans to whom the drug is administered include humans with an unstable tear film. More specific examples include dry eye patients or humans possibly infected with dry eye; patients having bacterial external ocular infection with dry eye (more specifically, bacterial keratoconjunctivitis) or humans possibly having bacterial external ocular infection with dry eye (more specifically, bacterial keratoconjunctivitis).

The administration (injection) amount of the aqueous liquid preparation of the present disclosure is not particularly limited, and is determined by the age, weight, sex, degree of symptoms, and method of administration of the subject to whom the aqueous liquid preparation is administered. For example, the dose of arbekacin can be about 0.004 to about 1.5 mg/kg body weight per day.

When the aqueous liquid preparation of the present disclosure is used as an ophthalmic solution, a few drops (e.g., one to three drops) may be dropped per each administration once or several times (e.g., two to eight times) a day. In one embodiment of the aqueous liquid preparation of the present disclosure, one drop per each administration is administered to eyes twice a day.

3. Treatment Method

The present disclosure includes a method for treating bacterial external ocular infection (more specifically, bacterial keratoconjunctivitis), comprising administering an aqueous liquid preparation comprising arbekacin and/or a salt thereof and at least one water-soluble polymer selected from the group consisting of hydroxypropyl methylcellulose, hydroxyethyl cellulose, methylcellulose, and polyvinylpyrrolidone to a subject in need thereof.

The present disclosure also includes a method for treating dry eye, comprising administering an aqueous liquid preparation comprising arbekacin and/or a salt thereof and at least one water-soluble polymer selected from the group consisting of hydroxypropyl methylcellulose, hydroxyethyl cellulose, methylcellulose, and polyvinylpyrrolidone to a subject in need thereof.

The present disclosure also includes a method for treating bacterial external ocular infection (more specifically, bacterial keratoconjunctivitis) with dry eye, comprising administering an aqueous liquid preparation comprising arbekacin and/or a salt thereof and at least one water-soluble polymer selected from the group consisting of hydroxypropyl methylcellulose, hydroxyethyl cellulose, methylcellulose, and polyvinylpyrrolidone to a subject in need thereof.

For the treatment methods described above, the description in section "2. Aqueous liquid preparation" can be used.

4. Method for Increasing Viscosity of Aqueous Liquid Preparation Containing Water-Soluble Polymer on Ocular Surface The present disclosure includes a method for increasing the viscosity of the aqueous liquid preparation containing a water-soluble polymer on an ocular surface, the method comprising administering to a subject in need an aqueous liquid preparation comprising arbekacin and/or a salt thereof and at least one water-soluble polymer selected from the group consisting of hydroxypropyl methylcellulose, hydroxyethyl cellulose, methylcellulose, and polyvinylpyrrolidone.

For the method for increasing the viscosity of the aqueous liquid preparation containing a water-soluble polymer on an ocular surface, the description in section "2. Aqueous liquid preparation" can be used.

5. Method for Enhancing Mucin Adhesion

The present disclosure includes a method for enhancing mucin adhesion, comprising administering to a subject in need an aqueous liquid preparation comprising arbekacin and/or a salt thereof and at least one water-soluble polymer selected from the group consisting of hydroxypropyl methylcellulose, hydroxyethyl cellulose, methylcellulose, and polyvinylpyrrolidone.

For the method for enhancing mucin adhesion, the description in section "2. Aqueous liquid preparation" can be used.

6. Method for Improving Transferability to Conjunctiva

The present disclosure comprises a method for improving the transferability of arbekacin and/or a salt thereof to the conjunctiva, comprising administering an aqueous liquid preparation comprising arbekacin and/or a salt thereof and at least one water-soluble polymer selected from the group consisting of hydroxypropyl methylcellulose, hydroxyethyl cellulose, methylcellulose, and polyvinylpyrrolidone to a subject in need thereof.

For the method for improving the transferability to the conjunctiva, the description in section "2. Aqueous liquid preparation" can be used.

7. Method for Stabilizing Tear Film

The present disclosure comprises a method for stabilizing a tear film, comprising administering to a subject in need an aqueous liquid preparation comprising arbekacin and/or a salt thereof and at least one water-soluble polymer selected from the group consisting of hydroxypropyl methylcellulose, hydroxyethyl cellulose, methylcellulose, and polyvinylpyrrolidone.

In the stabilization method described above, the description in section "2. Aqueous liquid preparation" can be used.

In this specification, the term "comprising" includes "consisting essentially of" and "consisting of." The present disclosure includes any and all combination of the components described in the present specification.

Various characteristics (properties, structures, functions, etc.) described in the above embodiments of the present disclosure may be combined in any manner to specify the subject matter included in the present disclosure. Specifically, the present disclosure includes all of the subject matter comprising any combination of the combinable properties described herein.

EXAMPLES

The disclosure is explained in detail using the following test examples. However, the present disclosure is not limited thereto. In the following, unless otherwise specified, experiments are conducted under atmospheric pressure and ambient temperature conditions. Unless otherwise specified, "%" means "mass % relative to volume.".

Test Example 1: Viscosity Measurement in the Presence of Mucin

With reference to the test method described in the literature (Emad Eldin Hassan and James M. Gallo, A Simple Rheological Method for the in Vitro Assessment of Mucin-Polymer Bioadhesive Bond Strength. *Pharmaceutical Research*, 1990, 7(5): Non-patent Literature 2), the viscosity obtained when a sample was mixed with a mucin solution was measured. The viscosity of each mixture was compared, and interaction of the sample and mucin was examined.

Samples

Preliminary solutions were mixed so that compositions shown in Table 1 were attained, thus preparing samples 1 to 11. Additionally, mucin (from porcine stomach, Type II, reagent, Sigma Aldrich) was dissolved in a 0.1M (mol/L) phosphate buffer to achieve a pH similar to that of tear fluid (neutral). The solution was adjusted to pH 7.0 with hydrochloric acid or sodium hydroxide, thus preparing a 6 w/v % mucin solution.

Method for Preparing Preliminary Solutions 25 w/v %, 16 w/v %, or 10 w/v % Arbekacin solution: Arbekacin sulfate was dissolved in purified water.
2.5 w/v % HPMC solution: Hypromellose 2208 (90SH-100SR, product compliant with Japanese Pharmacopoeia (JP), Shin-Etsu Chemical Co., Ltd.) was added and dispersed in heated, purified water (about 80° C.), followed by cooling to room temperature, and dissolution was confirmed.
1M phosphate buffer: A sodium dihydrogen phosphate hydrate (product compliant with JP, Fujifilm Wako Pure Chemicals Corporation) was dissolved in purified water, and the solution was adjusted to pH 7.0 with hydrochloric acid or sodium hydroxide.
0.1M phosphate buffer: A 1M phosphate buffer was diluted 1/10 with purified water.

Preheat time: 120 s
Measurement time: 90 s
Measuring temperature: 34° C.±0.1° C.
Rotation speed: 100 rpm Calculation Formula The viscosity increase value by the interaction of each sample and mucin was calculated according to the following formula.

$$\text{Viscosity increase value (mPa·s)} = (\eta_1 - \eta_2) - \eta_3$$

Viscosity increase value (mPa·s)=$(\eta_1-\eta_2)-\eta_3$
$\eta_1$: Viscosity of a mixture of each sample (1 mL) and a 6 w/v % mucin solution (1 mL)
$\eta_2$: Viscosity of a mixture of each sample (1 mL) and a 0.1 M phosphate buffer
$\eta_3$: Viscosity of a mixture of a 0.1M phosphate buffer (1 mL) and a 6 w/v % mucin solution (1 mL)

Evaluation of Interaction of Mucin and Sample

Samples A, B, and C are defined as follows.
A: Viscosity increase value (mPa·s) achieved by arbekacin
B: Viscosity increase value (mPa·s) achieved by HPMC
C: Viscosity increase value (mPa·s) achieved by arbekacin+HPMC.

It was evaluated that in the case of C−(A+B)>0, when the aqueous liquid preparation comprising arbekacin and HPMC was in contact with a mucin solution, a synergistic thickening effect was attained.

TABLE 1

| Amount (w/v %) | Number of samples | | | | | | | | | | |
|---|---|---|---|---|---|---|---|---|---|---|---|
| | 1 | 2 | 3 | 4 | 5 | 6 | 7 | 8 | 9 | 10 | 11 |
| Arbekacin sulfate (as arbekacin) | — | 0.5 | 2 | — | 0.5 | 2 | 3 | 3 | — | 0.1 | 3 |
| Hypromellose 2208 (90SH-100SR) | 0.8 | 0.8 | 0.8 | 1.4 | 1.4 | 1.4 | — | 1.4 | 2 | 2 | 2 |
| Sodium dihydrogen phosphate hydrate | | | | | 1.56 (0.1M) | | | | | | |
| Viscosity of each sample (mPa · s) | — | 6.63 | 7.11 | — | 23.17 | 21.91 | — | 9.05 | — | 72.31 | 22.73 |

Viscosity Measurement

The viscosity of each of the solutions, i.e., mixtures of each sample (1 mL) and a 6 w/v % mucin solution (1 mL), mixtures of each sample (1 mL) and a 0.1 M phosphate buffer, and a mixture of a 0.1M phosphate buffer (1 mL) and a 6 w/v % mucin solution (1 mL), was measured according to the following conditions.

Viscosity Measurement Conditions

Measuring device: TVE-25 viscometer (Toki Sangyo Co., Ltd.)
Rotor: 1°34'×R24 or 3°×R17.65 (the rotor was changed according to the viscosity to be measured)
Sample amount: 1.1 mL (when rotor 1°34'×R24 was used) or 0.8 mL (when rotor 3°×R17.65 was used)

Table 2 shows sample numbers used for calculating A, B, and C at each concentration of arbekacin and HPMC.

TABLE 2

| Arbekacin concentration (w/v %) | HPMC concentration (w/v %) | Number of samples used for calculating A, B, and C | | |
|---|---|---|---|---|
| | | A | B | C |
| 0.5 | 0.8 | 7 | 1 | 2 |
| 2 | 0.8 | 7 | 1 | 3 |
| 0.5 | 1.4 | 7 | 4 | 5 |
| 2 | 1.4 | 7 | 4 | 6 |
| 3 | 1.4 | 7 | 4 | 8 |
| 0.1 | 2 | 7 | 9 | 10 |
| 3 | 2 | 7 | 9 | 11 |

For the sample used for calculating A, the data of sample 7 (arbekacin 3% solution) were uniformly used regardless of the arbekacin concentration, because it was assumed that in a solution containing arbekacin alone, there was no significant difference in viscosity regardless of concentration.

Table 3 shows the results obtained by evaluating the viscosity increase value of each sample and interaction of each sample with mucin.

TABLE 3

| Arbekacin concentration (w/v %) | HPMC concentration (w/v %) | Number of samples for calculating Viscosity increase value (mPa · s) A | B | C | Interaction C − (A + B) |
|---|---|---|---|---|---|
| 0.5 | 0.8 | 7 / 0.07 | 1 / 0.05 | 2 / 0.24 | 0.12 |
| 2 | 0.8 | 7 / 0.07 | 1 / 0.05 | 3 / 0.25 | 0.13 |
| 0.5 | 1.4 | 7 / 0.07 | 4 / 2.34 | 5 / 3.38 | 0.97 |
| 2 | 1.4 | 7 / 0.07 | 4 / 2.58 | 6 / 3.38 | 0.73 |
| 3 | 1.4 | 7 / 0.07 | 4 / 2.40 | 8 / 3.12 | 0.65 |
| 0.1 | 2 | 7 / 0.07 | 9 / 5.86 | 10 / 6.72 | 0.79 |
| 3 | 2 | 7 / 0.07 | 9 / 6.05 | 11 / 7.10 | 0.98 |

When mucin and the mixture of arbekacin and HPMC were both present, the evaluation formula of interaction was C−(A+B)>0, indicating synergistic thickening. The synergistic thickening effect was observed in the range where arbekacin was 0.1 w/v % to 3 w/v % and HPMC was 0.8 w/v % to 2 w/v %. This indicated that interaction with mucin occurred only when arbekacin and HPMC were both present, resulting in thickening (enhancing mucin adhesion).

Interaction with mucin was compared using non-ionic water-soluble polymers other than hydroxypropyl methylcellulose.

Samples

Preliminary solutions were mixed so that the composition shown in Table 4 was achieved, thus preparing samples 12 to 19. The concentration of each water-soluble polymer solution was set so that a viscosity similar to that of 1.4 w/v % Hypromellose 2208 (90SH-100SR, product compliant with Japanese Pharmacopoeia (JP), Shin-Etsu Chemical Co.) solution was attained. Further, mucin (from porcine stomach, Type II, reagent, Sigma Aldrich) was dissolved in a 0.1M phosphate buffer so that a pH similar to that of tear fluid (neutral) was attained, and the solution was adjusted to pH 7.0 with hydrochloric acid or sodium hydroxide, thus preparing a 6 w/v % mucin solution.

Method for Preparing Preliminary Solutions 1 w/v % HEC solution: Hydroxyethylcellulose (product compliant with Japanese Pharmacopoeia (JP), Ashland, Inc.) was added and dissolved in heated (about 80° C.), purified water, followed by cooling to room temperature, and dissolution was confirmed.

1.6 w/v % MC solution: Methylcellulose (SM-400, product compliant with Japanese Pharmacopoeia (JP), Shin-Etsu Chemical Co.) was added and dispersed in heated (about 80° C.), purified water, followed by ice-cooling, and dissolution was confirmed.

5 w/v % PVP solution: Polyvinylpyrrolidone (Kollidon 90F, product compliant with Japanese Pharmacopoeia (JP), BASF SE) was dissolved in purified water.

30 w/v % PEG (polyethylene glycol) solution: Macrogol 6000 (product compliant with Japanese Pharmacopoeia (JP), NOF Corporation) was dissolved in purified water.

A 10 w/v % arbekacin solution, 1M phosphate buffer, and 0.1M phosphate buffer were prepared by the same methods as described above.

TABLE 4

| Amount (w/v %) | Number of samples 12 | 13 | 14 | 15 | 16 | 17 | 18 | 19 |
|---|---|---|---|---|---|---|---|---|
| Arbekacin sulfate (as arbekacin) | — | 1.5 | — | 1.5 | — | 1.5 | — | 1.5 |
| HEC | 0.4 | 0.4 | — | — | — | — | — | — |
| MC | — | — | 0.7 | 0.7 | — | — | — | — |
| PVP | — | — | — | — | 3.5 | 3.5 | — | — |
| PEG | — | — | — | — | — | — | 20 | 20 |
| Sodium dihydrogen phosphate hydrate | — | — | — | 1.56 (0.1M) | — | — | — | — |
| Viscosity of each sample (mPa · s) | — | 12.99 | — | 10.83 | — | 12.62 | — | 13.92 |

The viscosity was measured using the same method and conditions as described above to calculate the viscosity increase value.

Evaluation Regarding Interaction of Mucin and Sample

A, B, and C are defined as follows.
A: Viscosity increase value (mPa·s) achieved by arbekacin
B: Viscosity increase value (mPa·s) achieved by a water-soluble polymer
C: Viscosity increase value (mPa·s) achieved by arbekacin+a water-soluble polymer.

It was evaluated that in the case of C−(A+B)>0, when the aqueous liquid preparation comprising arbekacin and each water-soluble polymer was in contact with a mucin solution, a synergistic thickening effect was attained.

Table 5 shows sample numbers used for calculating A, B, and C at each concentration of arbekacin and a water-soluble polymer.

TABLE 5

| Arbekacin concentration (w/v %) | Name of water-soluble polymer/ Concentration of water-soluble polymer (w/v %) | Number of samples used for calculating A, B, and C A | B | C |
|---|---|---|---|---|
| 1.5 | HEC/0.4 | 7 | 12 | 13 |
| 1.5 | MC/0.7 | 7 | 14 | 15 |
| 1.5 | PVP/3.5 | 7 | 16 | 17 |
| 1.5 | PEG/20 | | *1 | |

*The sample became cloudy and could not be measured.

For the sample used for calculating A, the data of sample 7 (arbekacin 3% solution) were uniformly used regardless of the arbekacin concentration, because it was assumed that in a solution containing arbekacin alone, there was no significant difference in viscosity regardless of concentration.

Table 6 shows the results obtained by evaluating the viscosity increase value of each sample and interaction with mucin.

TABLE 6

| Arbekacin concentration (w/v %) | Name of water-soluble polymer/ Concentration of water-soluble polymer (w/v %) | Number of samples used for calculating Viscosity increase value (mPa·s) | | | Interaction C − (A + B) |
|---|---|---|---|---|---|
| | | A | B | C | |
| 1.5 | HEC/0.4 | 7 | 12 | 13 | 1.47 |
| | | 0.07 | 1.56 | 3.10 | |
| 1.5 | MC/0.7 | 7 | 14 | 15 | 1.47 |
| | | 0.07 | 1.38 | 2.92 | |
| 1.5 | PVP/3.5 | 7 | 16 | 17 | 1.24 |
| | | 0.07 | 2.03 | 3.34 | |
| 1.5 | PEG/20 | *2 | | | |

*The sample became cloudy and could not be measured.

Test Example 2: In Vitro Dialysis Membrane Test

The in vitro dialysis membrane test for confirming the release rate of arbekacin using a dialysis membrane was performed, with the aim of examining the interaction of mucin with the aqueous liquid preparation containing arbekacin and HPMC.

Samples

Required amounts of the preliminary solutions shown below were added to a 1.5-mL polypropylene tube, and pipetting was fully conducted with a micropipette, thus forming samples 20 to 27 (Table 7).

Method for Preparing Preliminary Solutions 25 w/v % and 16 w/v % arbekacin solutions: arbekacin sulfate was added and dissolved in purified water.

2.5 w/v % HPMC solution: Hypromellose 2208 (90SH-100SR, product compliant with JP, Shin-Etsu Chemical Co., Ltd.) was added and dispersed in heated (about 80° C.), purified water, followed by cooling to room temperature, and dissolution was confirmed. Phosphate Buffered Saline (PBS), pH 7.4: PBS Tablet (reagent, Takara Bio, Inc.) was added and dissolved in purified water.

2.5 w/v % and 5 w/v % Mucin solutions: Mucin (derived from porcine stomach, for biochemistry, Fujifilm Wako Pure Chemicals Corporation) was dissolved in PBS or water.

TABLE 7

Sample formulation used for dialysis membrane test

| Name of solution added | Number of samples | | | | | | | |
|---|---|---|---|---|---|---|---|---|
| | 20 | 21 | 22 | 23 | 24 | 25 | 26 | 27 |
| | Amount (w/v %) | | | | | | | |
| Arbekacin sulfate (as arbekacin) | 1 | 1 | 1 | 1 | 3 | 3 | 0.5 | 0.5 |
| Hypromellose 2208 (90SH-100SR) | 1 | 1 | — | — | 1.5 | — | 1.5 | — |
| Mucin (from porcine stomach) | 1 | — | 1 | — | 1 | — | 1 | — |

Test Method 1) 500 μL of a sample was sealed in a 2-mL volume glass container. The opening was covered with a dialysis membrane, and the surrounding area was fixed (the inside the glass container was the donor side). It was confirmed that the glass container and the dialysis membrane were firmly adhered. As the dialysis membrane, a commercially available product with the following specifications was used.

Fractional molecular weight: 12000 to 14000
Membrane material: regeneration cellulose.

2) 1) was attached to a beaker (outer liquid side) filled with PBS (15 mL) at a constant height from the bottom of the beaker, and the liquid in the beaker was stirred with a stirrer.

3) Using 1 mL of liquid sampled from the outer liquid side at any time between 15 and 240 minutes after the start of stirring as a sampling solution, the arbekacin content was measured according to the method described below. The remaining percentage, release rate, and the decrease percentage in the release rate of arbekacin were calculated according to the following formulae.

Calculation Formulae

The percentage of drug remaining in a donor relative to the theoretical total amount (%)=100−(cumulative amount of arbekacin released into the outer liquid by the time of sampling (μg)/theoretical total amount of arbekacin in the donor side (μg)×100)

Release rate (%/min): absolute value of the slope of the approximate line obtained by the least-squares method obtained when the percentage of remaining drug (%) and the sampling time (min) are respectively plotted on the y-axis and the x-axis for each sampling solution.

Decrease percentage in release rate (%): 100−(release rate of sample/release rate of an arbekacin solution alone×100)

Measurement of Arbekacin Amount

The sampling solutions were suitably diluted and measured by liquid chromatography (Ultimate 3000, Thermo Fisher Scientific, Inc.) under the following conditions.

Test Conditions

Detector: Charged aerosol detector Corona Veo RS
Column: Commercially available product comprising a stainless steel tube with an inner diameter of 4.6 mm and a length of 250 mm, and filled with 5 μm octylsilylated silica gel for liquid chromatography (Inertsil C8, 5 μm, 4.6 mm×250 mm, GL Sciences Inc.)
Column temperature: constant temperature around 30° C.
Mobile phase: gradient with a 5 mM heptafluorobutyric acid aqueous solution and a 5 mM heptafluorobutyric acid acetonitrile solution
Flow rate: 1.4 mL per minute Table 8 shows the percentage of arbekacin remaining at each time point, the release rate, and the decrease percentage in the release rate. FIG. 1 shows the release profile of each sample.

TABLE 8

Results of in vitro dialysis membrane test

| Number of samples | Sampling time Remaining percentage (%) | | | | | | Release rate (%/min) | Decrease percentage of release rate (%) |
|---|---|---|---|---|---|---|---|---|
| | 15 min. | 30 min. | 60 min. | 90 min. | 120 min. | 240 min. | | |
| 20 | 99.5 | 98.5 | 96.8 | 95.3 | 94.2 | 90.4 | 0.03963 | 38.8 |
| 21 | 99.4 | 98.3 | 96.0 | 94.0 | 92.3 | 85.3 | 0.06218 | 4.0 |
| 22 | 99.2 | 97.7 | 95.0 | 92.9 | 90.8 | 83.1 | 0.07047 | −8.8 |
| 23 | 99.4 | 98.1 | 96.0 | 93.9 | 91.9 | 84.7 | 0.06477 | — |
| 24 | — | 97.9 | 96.0 | — | 93.1 | 87.7 | 0.04780 | 25.5 |
| 25 | — | 98.0 | 96.1 | — | 92.8 | 84.5 | 0.06417 | — |
| 26 | — | 99.5 | 98.1 | — | 94.7 | 90.1 | 0.04487 | 42.5 |
| 27 | — | 98.8 | 96.4 | — | 91.5 | 82.4 | 0.07806 | — |

In the mixtures of arbekacin, HPMC, and mucin (samples 20, 24, and 26), the release rate was significantly reduced as compared to that of the arbekacin solution, and the decrease percentage was 25% or more. On the other hand, the decrease percentage in the release rate hardly changed in the mixture of arbekacin and HPMC (sample 21), and in the mixture of arbekacin and mucin (sample 22). The results indicated that when arbekacin alone or HPMC alone was mixed with mucin, interaction did not occur; however, interaction with mucin occurred only when both arbekacin and HPMC were contained. Specifically, this suggested that the mucin adhesion was enhanced by arbekacin and HPMC.

Test Example 3: Evaluation of Transferability to Conjunctiva

An aqueous liquid preparation containing arbekacin was administered to Japanese White rabbits as a single dose of ophthalmic solution, and the arbekacin concentration in the conjunctiva was evaluated.

Sample

Samples 28 and 29 were prepared as shown in Table 9.

TABLE 9

Formulation of sample used for evaluation of transferability to conjunctiva

| | Amount (w/v %) | |
|---|---|---|
| Name of components | Sample 28 | Sample 29 |
| Arbekacin sulfate (as arbekacin) | 3 | 3 |
| Hypromellose 2910 (HPMC; 60SH-10000) | 0.35 | — |
| Trometamol | 1.06 | 1.06 |
| Sodium thiosulfate hydrate | 0.5 | 0.5 |
| Concentrated benzalkonium chloride solution 50 | 0.04*[3] | 0.04*[3] |
| Hydrochloric acid | Suitable amount | Suitable amount |
| Sodium hydroxide | Suitable amount | Suitable amount |
| Purified water | Suitable amount | Suitable amount |
| pH | 7.0 | 7.0 |
| Osmotic pressure ratio | About 1 | About 1 |
| Viscosity (mPa · s) | 12.78 | 0.956 |

*[3]0.02 w/v % as benzalkonium chloride

Preparation Method

1) HPMC was added and dispersed in heated (about 80° C.), purified water, followed by cooling to room temperature, and dissolution was confirmed. The liquid was coarsely filtered through a 5-μm membrane filter to obtain a concentrated solution A of HPMC.

2) Trometamol, sodium thiosulfate hydrate, and arbekacin sulfate were added to purified water that had been separately prepared, and dissolved. The pH was adjusted to 7.0 by adding hydrochloric acid or sodium hydroxide to the solution, and a concentrated solution B comprising a mixture of components was obtained.

3) The concentrated solution B and a benzalkonium chloride solution were added to the concentrated solution A (used for preparation of sample 28) or purified water (used for preparation of sample 29), and stirred until complete dissolution.

4) Hydrochloric acid or sodium hydroxide was added thereto to adjust the pH to 7.0, and purified water was added until the prescribed amount was reached.

5) The solution obtained in 4) was sterilized by filtration using a 0.22-μm membrane filter to obtain an aqueous liquid preparation.

Matters Relating to Test System and the Like

Animal

Species: rabbit
Lineage: Japanese White species
Sex: Male
Weight range on arrival: about 2.00 to 2.49 kg
Number of rabbits used: 15

Matters Relating to Animal Experiment

Test Flow

The concentration in the conjunctiva after the aqueous liquid preparation containing arbekacin was administered to normal Japanese White rabbits (hereinafter referred to as rabbits) was evaluated. One of samples 28 and 29 was administered to eyes of each of the rabbits as a single dose. Euthanasia was performed 0.25, 0.5, and 1 hour after the administration, and eye tissue was collected. The number of examples was 3 eyes/sample/time point.

TABLE 10

| Animal | Sample | Number of examples/time point |
|---|---|---|
| Rabbit | Sample 28 (HPMC-containing 3% arbekacin ophthalmic solution) | 3 |
| Rabbit | Sample 29 (HPMC-free 3% arbekacin ophthalmic solution) | 3 |

Ophthalmic Administration

1) Each of the rabbits was held in place, and it was confirmed by naked-eye observation that the anterior eye part was not affected.
2) 35 μL of the sample was administered to eyes using a micropipette, and blinking was forcibly performed twice.
3) Each rabbit was released from the retention 30 minutes after the administration.

Euthanasia Treatment and Eye Tissue Collection

Euthanasia was performed 0.25, 0.5, and 1 hour after the administration, and eye tissue was collected.
1) Each of the rabbits was held in place, and euthanasia was performed with an overdose of sodium thiopental.
2) The ocular surface and the inside of the conjunctival sac were washed with a saline solution and wiped dry.
3) The eyelid was incised, and the eyeball including the conjunctiva was removed.
4) The conjunctiva and eyeball were collected.
5) The collected samples were frozen and stored in an ultra-low-temperature freezer.

Matters Relating to Analysis

The internal standard (IS) was kanamycin monosulfate, and the arbekacin concentration in the conjunctiva was analyzed using LC-MS/MS (Q TRAP 5500, AB SCIEX Pte., Ltd.) in positive ion mode.

Preparation of Solution 20 mM EDTA 0.672 g of disodium dihydrogen ethylenediamine tetraacetic acid dihydrate was collected. Subsequently, 100 mL of water was added thereto for dissolution.

Liquid for Dilution

Water/20 mM EDTA/formic acid (1000:2:1, v/v) and acetonitrile/formic acid (1000:1, v/v) were mixed at a ratio of 1:1.

IS Solution 2 mg of kanamycin monosulfate was weighed, and dissolved in 20 mL of 20% methanol. Subsequently, the solution was diluted with acetonitrile to 3.00 μg/mL.

Conjunctival Homogenate Preparation

1) The conjunctiva and water whose weight was four times the weight of the added conjunctiva were added to a tube containing twenty 3-mm zirconia beads.
2) The conjunctiva was crushed in a bead homogenizer to produce a 20% conjunctival homogenate.
Crushing conditions: 10 cycles each including crushing at 6000 rpm for 30 seconds and pausing for 30 seconds (set temperature: 4° C.)
3) A 20% conjunctival homogenate was diluted 2-fold with water to prepare a 10% conjunctival homogenate.

Blank Sample 1) 20 μL of a blank 10% conjunctival homogenate was collected.
2) 40 μL of acetonitrile was added.
3) 80 μL of acetonitrile was added and mixed.

Actual Sample 1) 20 μL of 10% conjunctival homogenate was collected.
2) 40 μL of acetonitrile was added.
3) 80 μL of an IS solution was added and mixed.

Pretreatment 1) 400 μL of a liquid for dilution was added and mixed.
2) Centrifugation was performed at 4° C., 20000× g for 10 minutes.
3) The supernatant was injected into LC-MS/MS.

Measurement Conditions

LC Conditions

Column: InertSustain Amide 3 μm UHPLC 2.1 I.D.×50 mm
Column temperature: 40° C.
Mobile phase: Gradient with water/20 mM EDTA/formic acid (1000:2:1, v/v) and acetonitrile/formic acid (1000:1, v/v)
Flow rate: 0.8 mL/min MS/MS Conditions Scan Type: MRM
Polarity: Positive
Ion Source: Turbo Spray

TABLE 11

| Analyte | Precursor ion (m/z) | Product ion (m/z) |
|---|---|---|
| Arbekacin | 553.237 | 425.200 |
| Kanamycin (IS) | 485.324 | 324.300 |

Evaluation of Transferability to Conjunctiva

An HPMC-containing 3% arbekacin ophthalmic solution (sample 28) with a viscosity of about 15 mPa·s (30° C.±0.1° C., preheat time: 0 s, rotation speed: 100 rpm, TVE-25 viscometer, cone rotor used: 3°×R17.65, measurement time: 90 s) was administered to rabbits as a single dose of an ophthalmic solution. Separately, an HPMC-free 3% arbekacin ophthalmic solution (sample 29) was administered to rabbits as a single dose of an ophthalmic solution. Tables 12 and 13 show detailed data on $C_{max}$ of the arbekacin concentration in the conjunctiva, and area under the concentration-time curve ($AUC_{0-t}$).

The maximum concentration of arbekacin in the conjunctiva ($C_{max}$) after the administration of the HPMC-containing 3% arbekacin ophthalmic solution (sample 28) and $AUC_{0-t}$ from time 0 to the final measurable time t were respectively 58.5 µg/g and 20.2 µg·h/g. In contrast, the $C_{max}$ of the arbekacin concentration in the conjunctiva after the administration of the HPMC-free 3% arbekacin ophthalmic solution (sample 29) and $AUC_{0-t}$ were respectively 17.0 µg/g and 10.5 µg·h/g. This indicated that the HPMC-containing preparation had a $C_{max}$ about 3.4 times and $AUC_{0-t}$ about 1.9 times higher than those of the HPMC-free preparation. This suggested that the incorporation of HPMC in the arbekacin ophthalmic solution prolonged the retention time of the arbekacin ophthalmic solution on the ocular surface, which increased the arbekacin concentration in the conjunctiva. In this regard, a comparison of the transferability of a sodium cromoglicate ophthalmic solution containing hydroxypropyl methylcellulose to the conjunctiva between a non-viscous preparation and a highly viscous preparation (580 mPa·s) showed that the $C_{max}$ was 2.1 times higher in the highly viscous preparation (580 mPa·s) (Non-patent Literature 9). Despite the viscosity of the HPMC-containing preparation (sample 28) being about ⅕ of that of the preparation described in the literature above, the $C_{max}$ was 3.4 times higher; an increase in transferability more than expected was confirmed. The incorporation of HPMC in the arbekacin ophthalmic solution allowed for interaction with mucin, and attained excellent mucin adhesion in addition to an excellent thickening effect, thus improving transferability.

TABLE 12

Outline of the arbekacin concentration in the conjunctiva after single eye administration to rabbits

| Sample | Sampling time (h) | Concentration in conjunctiva (µg/g) Average value | Standard deviation | Number of Examples |
|---|---|---|---|---|
| Sample 28 | 0.25 | 58.5 | 38.8 | 3 |
| Sample 28 | 0.5 | 11.1 | 9.5 | 3 |
| Sample 28 | 1 | 5.65 | 3.30 | 3 |
| Sample 29 | 0.25 | 17.0 | 15.1 | 3 |
| Sample 29 | 0.5 | 10.7 | 8.8 | 3 |
| Sample 29 | 1 | 8.71 | 10.2 | 3 |

Sample 28: HPMC-containing 3% arbekacin ophthalmic solution
Sample 29: HPMC-free 3% arbekacin ophthalmic solution

TABLE 13

Pharmacokinetic parameter of arbekacin in the conjunctiva after single eye administration to rabbits

| Sample | $C_{max}$ (µg/g) | $AUC_{0-t}$ (µg·h/g) | $T_{max}$ (h) |
|---|---|---|---|
| Sample 28 | 58.5 | 20.2 | 0.25 |
| Sample 29 | 17.0 | 10.5 | 0.25 |

$T_{max}$: Time to reach maximum concentration

The invention claimed is:

1. An aqueous liquid preparation comprising
   arbekacin and/or a salt thereof and
   hydroxypropyl methylcellulose,
   wherein
   the aqueous liquid preparation is an ophthalmic solution,
   the total concentration of the arbekacin and/or a salt thereof is about 0.1 w/v % to about 3.0 w/v %, and
   the concentration of the hydroxypropyl methylcellulose is about 0.8 w/v % to about 2 w/v %.

2. The aqueous liquid preparation according to claim 1, wherein the mass ratio of the total content of the arbekacin and/or a salt thereof to the content of the hydroxypropyl methylcellulose is in the range of about 1:0.04 to about 1:70.

3. An aqueous liquid preparation comprising arbekacin and/or a salt thereof and hydroxypropyl methylcellulose, wherein
   the total concentration of the arbekacin and/or a salt thereof is about 0.1 w/v % to about 3.0 w/v %;
   the concentration of the hydroxypropyl methylcellulose is about 0.8 w/v % to about 2.0 w/v %;
   the mass ratio of the total content of the arbekacin and/or a salt thereof to the content of the hydroxypropyl methylcellulose is in the range of about 1:0.04 to about 1:70, and
   the aqueous liquid preparation is an ophthalmic solution.

4. The aqueous liquid preparation according to claim 1, wherein the aqueous liquid preparation has a viscosity of about 5 to about 50 mPa·s.

5. A method for improving transferability of arbekacin to the conjunctiva, the method comprising administering an effective amount of the aqueous liquid preparation according to claim 1 to a subject in need thereof.

6. A method for treating a bacterial external ocular infection, the method comprising administering an affective amount of the aqueous liquid preparation according to claim 1 to a subject in need thereof.

7. A method for stabilizing tear film, the method comprising administering an effective amount of the aqueous liquid preparation according to claim 1 to a subject in need thereof.

8. A method for treatment of a bacterial external ocular infection with dry eye, the method comprising administering an effective amount of the aqueous liquid preparation according to claim 1 to a subject in need thereof.

9. A method for treating bacterial conjunctivitis, the method comprising administering an effective amount of the aqueous liquid preparation according to claim 1 to a subject in need thereof.

10. The aqueous liquid preparation according to claim 1, wherein the aqueous liquid preparation does not comprise bromfenac or its pharmacologically acceptable salt.

11. The aqueous liquid preparation according to claim 1, wherein the aqueous liquid preparation does not comprise povidone iodine.

\* \* \* \* \*